US011999806B2

(12) United States Patent
Zhou et al.

(10) Patent No.: US 11,999,806 B2
(45) Date of Patent: Jun. 4, 2024

(54) BROAD-SPECTRUM POLYPEPTIDE AGAINST ENTEROVIRUS AND APPLICATION THEREOF

(71) Applicants: WUHAN INSTITUTE OF VIROLOGY, CHINESE ACADEMY OF SCIENCES, Hubei (CN); FUDAN UNIVERSITY, Shanghai (CN)

(72) Inventors: Xi Zhou, Wuhan (CN); Lu Lu, Shanghai (CN); Yuan Fang, Wuhan (CN); Shibo Jiang, Shanghai (CN); Zezhong Liu, Shanghai (CN); Chengfeng Qin, Beijing (CN); Yang Qiu, Wuhan (CN); Jingfang Mu, Wuhan (CN)

(73) Assignees: WUHAN INSTITUTE OF VIROLOGY, CHINESE ACADEMY OF SCIENCES, Hubei (CN); FUDAN UNIVERSITY, Shanghai (CN)

( * ) Notice: Subject to any disclaimer, the term of this patent is extended or adjusted under 35 U.S.C. 154(b) by 888 days.

(21) Appl. No.: 16/963,196

(22) PCT Filed: Jan. 21, 2019

(86) PCT No.: PCT/CN2019/072455

§ 371 (c)(1),
(2) Date: Jul. 17, 2020

(87) PCT Pub. No.: WO2019/141263

PCT Pub. Date: Jul. 25, 2019

(65) Prior Publication Data

US 2023/0192769 A1 Jun. 22, 2023

(30) Foreign Application Priority Data

Jan. 20, 2018 (CN) ......................... 201810056297.1

(51) Int. Cl.

*A61K 38/00* (2006.01)
*A61P 31/14* (2006.01)
*C07K 7/08* (2006.01)

(52) U.S. Cl.

CPC ................ *C07K 7/08* (2013.01); *A61P 31/14* (2018.01); *A61K 38/00* (2013.01)

(58) Field of Classification Search

None

See application file for complete search history.

(56) References Cited

U.S. PATENT DOCUMENTS

2016/0376562 A1 12/2016 Venskus et al.

FOREIGN PATENT DOCUMENTS

| | | | |
|---|---|---|---|
| CN | 105394045 | A | 3/2016 |
| CN | 105518128 | A | 4/2016 |
| CN | 106668832 | A | 5/2017 |

OTHER PUBLICATIONS

PCT International Search Report, PCT/CN2019/072455, Apr. 19, 2019, 19 Pages.

Zhang, Xiaokang et al., "Advances in Research on Anti-intestinal Virus Target Drugs," Chinese Medicinal Biotechnology, vol. 11, No. 5, Oct. 30, 2016, p. 451, left column, paragraph 1, and p. 454, left column, paragraphs 2-4.

Gonzalez-Magaldi, M. et al, "Peptides Interfering 3A Protein Dimerization Decrease FMDV Multiplication," PLOS ONE, vol. 10, No. 10, Oct. 27, 2015, abstract.

Chien, Y.S. et al., "Polyprotein [Coxsackievirus A6], GenBank: ATP75734.1," NCBI, Nov. 6, 2017, FEATURES part.

Tang, Rui et al., "Screening Protein Interacted with Enterovirus 71 3A Protein by Means of T7-phage Display System," International Journal of Medicine, vol. 35, No. 16, Aug. 31, 2014, pp. 2129-2131.

Gao, Q. Q. et al., "Discovery of Itraconazole with Broad-Spectrum in Vitro Antienterovirus Activity that Targets Nonstructural Protein 3A," Antimicrobial Agents and Chemotherapy, vol. 59, No. 5, May 31, 2015, pp. 2654-2665.

*Primary Examiner* — Thomas S Heard

(74) *Attorney, Agent, or Firm* — Kilpatrick Townsend & Stockton LLP

(57) ABSTRACT

Provided are a series of polypeptides with antiviral activity. The present invention provides a new strategy for preventing and controlling Enterovirus such as EV71, CVA16, CVA6, CVB3, and CVB5 viruses and provides a new theoretical basis for accelerating the research and development of a polypeptide small molecule drug against Enterovirus such as EV71, CVA16, CVA6, CVB3, and CVB5 viruses.

9 Claims, 15 Drawing Sheets

Specification includes a Sequence Listing.

SEQUENCE LISTING

```
<160> NUMBER OF SEQ ID NOS: 14

<210> SEQ ID NO 1
<211> LENGTH: 15
<212> TYPE: PRT
<213> ORGANISM: Artificial Sequence
<220> FEATURE:
<223> OTHER INFORMATION: Polypeptide EP

<400> SEQUENCE: 1

Glu Glu Val Arg Gln Tyr Cys Arg Glu Gln Gly Trp Ile Ile Pro
1               5                   10                  15


<210> SEQ ID NO 2
<211> LENGTH: 18
<212> TYPE: PRT
<213> ORGANISM: Artificial Sequence
<220> FEATURE:
<223> OTHER INFORMATION: Polypeptide P2

<400> SEQUENCE: 2

Arg Arg Arg Arg Arg Arg Arg Arg Glu Glu Val Arg Gln Tyr Cys Arg
1               5                   10                  15

Asp Gln


<210> SEQ ID NO 3
<211> LENGTH: 29
<212> TYPE: PRT
<213> ORGANISM: Artificial Sequence
<220> FEATURE:
```

-continued

<223> OTHER INFORMATION: Polypeptide 3A-TAT-EP

<400> SEQUENCE: 3

Tyr Gly Arg Lys Lys Arg Arg Gln Arg Arg Arg Gly Ser Gly Glu Glu
1 5 10 15

Val Arg Gln Tyr Cys Arg Glu Gln Gly Trp Ile Ile Pro
20 25

<210> SEQ ID NO 4
<211> LENGTH: 28
<212> TYPE: PRT
<213> ORGANISM: Artificial Sequence
<220> FEATURE:
<223> OTHER INFORMATION: Polypeptide 3A-EP-DRI (D-amino acid)
<220> FEATURE:
<221> NAME/KEY: Modified
<222> LOCATION: (1)..(1)
<223> OTHER INFORMATION: N terminal acetylated

<400> SEQUENCE: 4

Pro Ile Ile Trp Gly Gln Glu Arg Cys Tyr Gln Arg Val Glu Glu Pro
1 5 10 15

Pro Arg Arg Arg Gln Arg Arg Lys Lys Arg Gly Tyr
20 25

<210> SEQ ID NO 5
<211> LENGTH: 15
<212> TYPE: PRT
<213> ORGANISM: Artificial Sequence
<220> FEATURE:
<223> OTHER INFORMATION: Polypeptide 3A-EP-PEG4-PA
<220> FEATURE:
<221> NAME/KEY: Modified
<222> LOCATION: (15)..(15)
<223> OTHER INFORMATION: C terminal AK-PEG4-K-C16

<400> SEQUENCE: 5

Glu Glu Val Arg Gln Tyr Cys Arg Glu Gln Gly Trp Ile Ile Pro
1 5 10 15

<210> SEQ ID NO 6
<211> LENGTH: 16
<212> TYPE: PRT
<213> ORGANISM: Artificial Sequence
<220> FEATURE:
<223> OTHER INFORMATION: Polypeptide P1

<400> SEQUENCE: 6

Arg Arg Arg Arg Arg Arg Arg Arg Ala Ile Ser Asp Leu Leu Ala Ser
1 5 10 15

<210> SEQ ID NO 7
<211> LENGTH: 16
<212> TYPE: PRT
<213> ORGANISM: Artificial Sequence
<220> FEATURE:
<223> OTHER INFORMATION: Polypeptide CR

<400> SEQUENCE: 7

Tyr Gly Arg Lys Lys Arg Arg Gln Arg Arg Arg Gly Ser Gly Cys Arg
1 5 10 15

<210> SEQ ID NO 8
<211> LENGTH: 15
<212> TYPE: PRT
<213> ORGANISM: Artificial Sequence
<220> FEATURE:

<223> OTHER INFORMATION: Polypeptide EP-PA
<220> FEATURE:
<221> NAME/KEY: Modified
<222> LOCATION: (15)..(15)
<223> OTHER INFORMATION: C terminal AK-C16(palmitic acid (C16:0))

<400> SEQUENCE: 8

Glu Glu Val Arg Gln Tyr Cys Arg Glu Gln Gly Trp Ile Ile Pro
1 5 10 15

<210> SEQ ID NO 9
<211> LENGTH: 15
<212> TYPE: PRT
<213> ORGANISM: Artificial Sequence
<220> FEATURE:
<223> OTHER INFORMATION: Polypeptide EP-CHOL
<220> FEATURE:
<221> NAME/KEY: Modified
<222> LOCATION: (15)..(15)
<223> OTHER INFORMATION: C terminal AK-Chol(cholesterol)

<400> SEQUENCE: 9

Glu Glu Val Arg Gln Tyr Cys Arg Glu Gln Gly Trp Ile Ile Pro
1 5 10 15

<210> SEQ ID NO 10
<211> LENGTH: 22
<212> TYPE: PRT
<213> ORGANISM: Artificial Sequence
<220> FEATURE:
<223> OTHER INFORMATION: Polypeptide ER

<400> SEQUENCE: 10

Tyr Gly Arg Lys Lys Arg Arg Gln Arg Arg Arg Gly Ser Gly Glu Glu
1 5 10 15

Val Arg Gln Tyr Cys Arg
20

<210> SEQ ID NO 11
<211> LENGTH: 21
<212> TYPE: PRT
<213> ORGANISM: Artificial Sequence
<220> FEATURE:
<223> OTHER INFORMATION: Polypeptide ER-DRI (D-amino acid)
<220> FEATURE:
<221> NAME/KEY: Modified
<222> LOCATION: (1)..(1)
<223> OTHER INFORMATION: N terminal acetylated

<400> SEQUENCE: 11

Arg Cys Tyr Gln Arg Val Glu Glu Pro Pro Arg Arg Arg Gln Arg Arg
1 5 10 15

Lys Lys Arg Gly Tyr
20

<210> SEQ ID NO 12
<211> LENGTH: 22
<212> TYPE: PRT
<213> ORGANISM: Artificial Sequence
<220> FEATURE:
<223> OTHER INFORMATION: Polypeptide BP-8

<400> SEQUENCE: 12

Tyr Gly Arg Lys Lys Arg Arg Gln Arg Arg Arg Gly Ser Gly Glu Ala
1 5 10 15

Val Arg Glu Tyr Cys Lys
20

-continued

```
<210> SEQ ID NO 13
<211> LENGTH: 24
<212> TYPE: PRT
<213> ORGANISM: Artificial Sequence
<220> FEATURE:
<223> OTHER INFORMATION: Polypeptide BP-10

<400> SEQUENCE: 13

Tyr Gly Arg Lys Lys Arg Arg Gln Arg Arg Arg Gly Ser Gly Glu Ala
1               5                   10                  15

Val Arg Glu Tyr Cys Lys Glu Lys
            20


<210> SEQ ID NO 14
<211> LENGTH: 29
<212> TYPE: PRT
<213> ORGANISM: Artificial Sequence
<220> FEATURE:
<223> OTHER INFORMATION: Polypeptide BP-15

<400> SEQUENCE: 14

Tyr Gly Arg Lys Lys Arg Arg Gln Arg Arg Arg Gly Ser Gly Glu Ala
1               5                   10                  15

Val Arg Glu Tyr Cys Lys Glu Lys Gly Trp Leu Val Pro
            20                  25
```

BROAD-SPECTRUM POLYPEPTIDE AGAINST ENTEROVIRUS AND APPLICATION THEREOF

CROSS REFERENCE TO RELATED APPLICATIONS

This application is the National Stage of Application No. PCT/CN2019/072455, filed Jan. 21, 2019, which claims the priority of Chinese patent application No. 2018100562971 filed with the Chinese Patent Office on Jan. 20, 2018, entitled "INHIBITOR OF ENTEROVIRUS 71 AND APPLICATION THEREOF", each of which is incorporated herein by reference in its entirety.

SEQUENCE LISTING

The instant application contains a Sequence Listing which has been submitted via EFS-Web and is hereby incorporated by reference in its entirety. Said ASCII copy, created on Feb. 19, 2021, is named 46761US_sequencelisting.txt, and is 4,889 bytes in size.

BACKGROUND

The invention relates to the field of biomedicine, and in particular to a polypeptide against various enterovirus and applications thereof.

SUMMARY

Enterovirus is a positive-sense single-stranded RNA virus, and belongs to the Enterovirus genus of the Picornaviridae family, mainly including human Enterovirus (EV), Coxsackie A virus (CVA), Coxsackie B virus (CVB), Echovirus, Rhinovirus, and Poliovirus. Enterovirus infections are widely distributed around the world and exhibit complex and diverse clinical manifestations, ranging from mild fever, fatigue, respiratory diseases, to herpes angina, hand-foot-and-mouth disease, and to severe aseptic meningitis, myocarditis, encephalitis, poliomyelitis, etc. At present, there is a lack of specific drugs that can effectively treat or prevent enterovirus infections.

Herpetic angina is mainly caused by Coxsackievirus Group A type 2 (CVA2), CVA4, CVA6, CVA9, CVA16, CVA22, and Coxsackievirus group B type 1 (CVB1), CVB2, CVB3, CVB4, or CVB5. Herpetic angina often causes fever, and the temperature is mostly not high or moderate. Occasionally, the fever is as high as 40° C. or even causing convulsions. The fever may last about 2 to 4 days. Older children may complain of sore throat, which can affect swallowing. Infants and young children may show salivation, refusal to eat, and restlessness. Sometimes it is accompanied by headache, abdominal pain or myalgia. About 25% of children under 5 years old with herpetic angina may be accompanied by vomiting. The patient may show typical symptoms in the pharynx, including pharyngeal hyperemia, and several (from 1 to 2 up to more than 10) small (1-2 mm in diameter) gray-white herpes surrounded by redness in the oral mucosa within 2 days of onset. After 2 to 3 days, the redness increases and the herpes rupture to form a yellow ulcer. This mucosal rash is more common in the anterior column of the tonsils, but also in the soft palate, uvula, and tonsils, but does not involve the gums and buccal mucosa. The course of the disease is usually 4 to 6 days, occasionally extended to 2 weeks.

Hand-foot-and-mouth disease is mainly caused by enterovirus 71 (EV71), CVA6, CVA8, CVA10, CVA16, CVB3 and CVB5. The common clinical manifestations of hand-foot-and-mouth disease include acute fever, mouth pain, anorexia, and scattered herpes or ulcers in the oral mucosa, mostly on the tongue, buccal mucosa, and hard palate, and also affecting soft palate, gums, tonsils and pharynx. Maculopapular rashes appear in the hands, feet, buttocks, arms and legs, and then turn into herpes which are surrounded by inflammatory redness and contains less fluid in the blister. Typically, there are more rashes on the hands and feet, both on the dorsum and the vola, from a few to dozens, and after subsided, they leaves no traces and no pigmentation. Some children with hand-foot-and-mouth disease have herpetic angina as the first symptom, and then red rashes in the palm, sole, buttocks and other parts. When the course of the disease develops rapidly, a small number of children can develop from hand-foot-and-mouth disease to severe aseptic meningitis and encephalitis, manifested as fever, headache, nausea, vomiting, and then meningeal irritation, as well as body temperature fluctuations with low-grade fever in the most case and sometimes with fever up to 40° C. or more, often bimodal fever in the course of the disease. Other symptoms include such as sore throat, muscle aches, skin rash, photophobia, diarrhea, swollen lymph nodes, and sometimes mild paralysis.

Myocarditis is mainly caused by CVB1-61 and Echovirus. Depend on the extent and location of the disease, the clinical manifestations of patients with viral myocarditis include asymptomatic case in mild case to heart failure, cardiogenic shock and sudden death in severe case. Patients often have a history of upper respiratory or intestinal infections 1 to 3 weeks before the onset of symptoms, manifested as fever, body aches, sore throat, fatigue, nausea, vomiting, diarrhea and other symptoms, and then palpitations, chest tightness, chest pain or precordial pain, dizziness, dyspnea, edema, and even Adams-Stokes syndrome, and in some patients, heart failure or cardiogenic shock.

Enterovirus is a positive-sense single-stranded RNA virus, which has a genome of about 7.5 kb, containing a large ORF encoding a polyprotein. The polyprotein can be further hydrolyzed into 4 structural proteins (VP1-VP4) and 7 nonstructural proteins (2A-2C and 3A-3D). In enteroviruses (including EV71, CVA and CVB), protein 3A is an extremely conserved nonstructural protein, which exists in the form of homodimers in the intracellular membrane and plays an important role in the replication of viruses and the regulation of host innate immunity.

After being infected by the virus, the host cell will activate a series of natural immune mechanisms, including RNA interference (RNAi)-mediated antiviral immunity. After the virus infects the host cell, due to the structure of the virus genome or replication intermediates, long double-stranded RNA (dsRNA) derived from the virus will be produced. These dsRNAs are recognized by the host Dicer protein and cleaved into viral small interfering RNA (vsiRNA). Then, vsiRNA binds with Argonaute (AGO) protein to form RNA-induced silencing complex (RISC), which ultimately mediates the degradation of the viral target gene RNA, thereby inhibiting the replication of the virus to eliminate the virus.

BRIEF DESCRIPTION OF THE INVENTION

In view of this, the present invention provides a polypeptide and application thereof.

In order to achieve the above-mentioned purpose of the invention, the present invention provides the following technical solutions.

The present invention provides use of enterovirus RNA suppressing protein (ERSP) as a target in the preparation of a medicine for preventing and/or treating viral diseases.

The present invention also provides use of a polypeptide in the preparation of an inhibitor of ERSP, wherein the function of ERSP is inhibited by the polypeptide, and the viral nucleic acid is cut by Dicer (endoribonuclease Dicer) to produce viral small interfering RNA (vsiRNA).

The invention also provides use of a polypeptide in the preparation of a medicine for preventing and treating viral diseases.

In some specific embodiments of the present invention, the ERSP is enterovirus nonstructural protein 3A.

In some specific embodiments of the present invention, the enterovirus belongs to the Picornaviridae enterovirus genus, including human Enterovirus (EV), Coxsackie A virus (CVA), Coxsackie B virus (CVB), Echovirus, Rhinovirus, and Poliovirus.

In some specific embodiments of the present invention, the viral diseases include hand-foot-and-mouth disease, myocarditis, herpes angina, aseptic meningitis, encephalitis and viral cold.

In some specific embodiments of the present invention, the amino acid sequence of the polypeptide comprises CR, CK and/or DLL.

In some specific embodiments of the present invention, the polypeptide has a sequence selected from:

I. (X1) (X2)DLL, (X2)DLL(X3), DLL(X3) (X4), (X5) YC(X6), C(X6), wherein,

X1 is isoleucine (I),

X2 is selected from serine (S) or alanine (A),

X3 is selected from alanine (A) or lysine (K) or glutamine (Q) or arginine (R) or serine (S) or cysteine (C), X4 is selected from serine (S) or alanine (A), X5 is selected from glutamic acid (E) or glutamine (Q), X6 is selected from arginine (R) or lysine (K); or II. a sequence with deletion, addition or substitution of at least one amino acid in the sequence in I; or III. a sequence inhibiting the activity of ERSP and having at least 50% homology to the sequence in I or II; or IV. the complementary sequence of the sequence in I or II or III.

The "amino acid" in the present invention includes natural amino acids or unnatural amino acids. Amino acid types well known to those skilled in the art are within the scope of the present invention.

In some specific embodiments of the present invention, the sequences of I is as shown in any one of SEQ ID NOs: 1-14, without the sequence of cell-penetrating peptide and the sequence of peptide linker.

The present invention also provides a polypeptide capable of inhibiting the activity of ERSP.

In some specific embodiments of the present invention, the amino acid sequence of the polypeptide comprises CR, CK and/or DLL.

In some specific embodiments of the present invention, the amino acid sequence of the polypeptide comprises YCR and/or YCK.

In some specific embodiments of the present invention, the polypeptide has a sequence selected from:

I. (X1) (X2)DLL, (X2)DLL(X3), DLL(X3) (X4), (X5) YC(X6), C(X6), wherein,

X1 is isoleucine (I),

X2 is selected from serine (S) or alanine (A),

X3 is selected from alanine (A) or lysine (K) or glutamine (Q) or arginine (R) or serine (S) or cysteine (C), X4 is selected from serine (S) or alanine (A), X5 is selected from glutamic acid (E) or glutamine (Q), X6 is selected from arginine (R) or lysine (K); or II. a sequence with deletion, addition or substitution of at least one amino acid in the sequence in I; or III. a sequence inhibiting the activity of ERSP and having at least 50% homology to the sequence in I or II; or IV. the complementary sequence of the sequence described in I or II or III.

In some specific embodiments of the present invention, the sequence of the polypeptide in I is as shown in any one of SEQ ID NOs: 1-14, without the sequence of penetrating peptide and the sequence of peptide linker.

On this basis, the present invention also provides a nucleic acid having a nucleotide sequence encoding the polypeptide.

The present invention also provides a recombinant vector comprising the nucleic acid.

On this basis, the present invention also provides a host cell comprising the recombinant vector.

The present invention also provides a medicine comprising the polypeptide and pharmaceutically acceptable excipients.

The present invention also provides a vaccine comprising the polypeptide and pharmaceutically acceptable excipients.

The invention also provides a method for treating enterovirus infections comprising oral administration or injection of the medicine to a subject in need thereof, wherein the injection is intramuscular injection, intraperitoneal injection or intravenous injection.

The present invention also provides a method for preventing enterovirus infections comprising administration of the vaccine to a subject in need thereof.

In the present invention, the term "prevent", "preventing" or "prevention" means that various methods or measures for preventing the occurrence or development of diseases, including medical, physical or chemical methods for preventing or reducing the occurrence or development of various symptoms of diseases are performed before the occurrence of diseases confirmed by clinical standards.

In the present invention, the term "treat", "treating" or "treatment" means that various methods or measures are performed to prevent and reduce the occurrence or development of the disease, inhibit, suppress, reduce, improve, slow down, stop, delay or reverse the development or aggravation of the disease course, alleviate or reduce various indicators, including symptoms or complications of diseases, disorders or conditions, or cure or eliminate diseases, disorders or conditions.

In the present invention, the term "medicine" refers to a single compound, a composition of multiple compounds, or a composition or formulation with a single compound as the main active ingredient, or a composition or formulation with multiple compounds as active ingredients, which can be used to prevent or treat a certain disease. A "medicine" should be understood as not only to refer to a product approved for production by the administrative agency in accordance with the laws and regulations of a country, but also to refer to various material forms formed with a single compound as the active ingredient in order to achieve the approval for production. "Formed" should be understood as obtaining through chemical synthesis, biological transformation or purchase.

The present invention also provides an inhibitor of enterovirus 71, wherein the inhibitor is polypeptide P2 with the amino acid sequence shown in SEQ ID NO: 2.

The present invention also provides variants of the inhibitor, wherein the variant is 3A-TAT-EP with the amino acid sequence as shown in SEQ ID NO: 3, 3A-EP-DRI with the amino acid sequence as shown in SEQ ID NO: 4, or 3A-EP-PEG4-PA with the amino acid sequence as shown in SEQ ID NO: 5.

In addition, the present invention also provides use of the inhibitor or the variants in the preparation of an inhibitor of enterovirus.

RNA interference is an antiviral immune mechanism. In the antiviral process with RNA interference, the double-stranded RNA produced during viral RNA replication is recognized by the host Dicer protein and cleaved into small interfering RNA (siRNA). These virus-derived small interfering RNAs (vsiRNAs) are transferred and assembled into RNA-induced silencing complexes, which mediate the degradation of homologous viral RNA to achieve antiviral goals. For example, the nonstructural protein 3A of EV71 can bind to the viral double-stranded RNA to prevent it from being cut by Dicer, and thus inhibit the production of virus-derived small interfering RNAs (vsiRNAs), so as to achieve the purpose of escaping from the host anti-viral mechanism via RNA interference.

The present invention provides a series of polypeptides with antiviral activity. The present invention provides a new strategy for preventing and controlling enterovirus such as EV71, CVA16, CVA6, CVB3, and CVB5 viruses and provides a new theoretical basis for accelerating the research and development of a polypeptide small molecule drug against enterovirus such as EV71, CVA16, CVA6, CVB3, and CVB5 viruses.

DETAILED DESCRIPTION

Figure 1A:
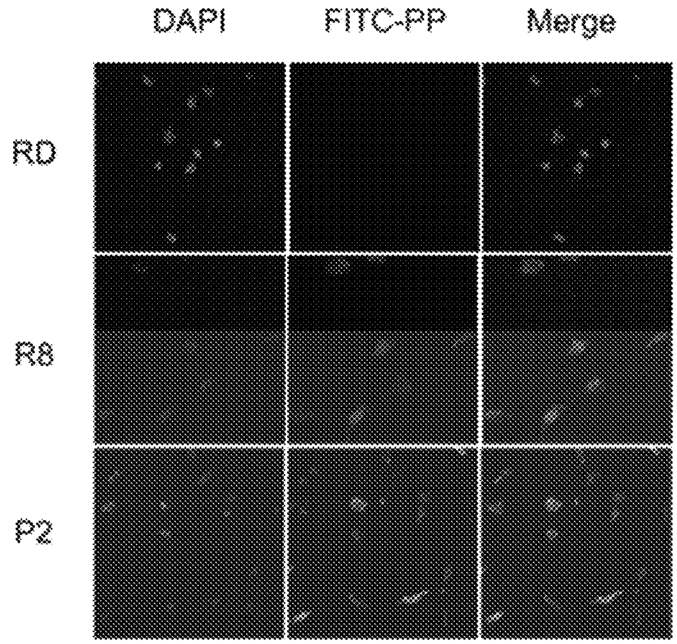
FIGS. 1A-1B show the detection of the ability of polypeptide P2 to penetrate the cell membrane and enter the cytoplasm by fluorescent labeling.

The present invention discloses polypeptides and uses thereof. Those skilled in the art can learn from the contents of the present invention and appropriately improve the process parameters. It is to be understood that all such alternatives and modifications are obvious to those skilled in the art and are considered to be included in the present invention. The method and the application of the present invention have been described according to the preferred embodiments, and it is obvious that the method and application described herein may be changed or appropriately modified and combined without departing from the content, spirit and scope of the present invention.

The EV71 3A protein contains 86 amino acid residues. Protein 3A has the ability to form dimer, and its dimerization plays a key role in the proper functioning of 3A. Based on the composition and sequence characteristics of the two helical structures of the dimerization domain of protein 3A, the applicant designed polypeptide EP (shown in SEQ ID NO: 1), which can bind to the EV71 nonstructural protein 3A and interfere with the dimer formation of protein 3A, thereby inhibiting virus replication and infection.

In order to allow the inhibitor to penetrate the cell membrane and enter the cell to inhibit viruses, polypeptide P2 (SEQ ID NO: 2) is designed using polypeptide EP as the core sequence. P2 polypeptide is capable of competing with al, thereby preventing dimerization of 3A, inhibiting the function of 3A in anti-innate immunity, and finally achieving anti-viral purposes.

Based on P2, a series of variants are constructed according to the modification of P2. It is shown by experiments that the variants of P2 have improved ability to inhibit viruses, which gives great significance to the prevention and treatment of diseases caused by enteroviruses.

The variants include 3A-TAT-EP with the amino acid sequence as shown in SEQ ID NO: 3, 3A-EP-DRI with the amino acid sequence as shown in SEQ ID NO: 4, and 3A-EP-PEG4-PA with the amino acid sequence as shown in SEQ ID NO: 5.

The present invention also provides uses of the inhibitor of enterovirus 71, comprising preparing the inhibitor of enterovirus 71 using polypeptide P2 or the variants of polypeptide P2, or preparing the inhibitor of enterovirus 71 using polypeptide P2 or the variants of polypeptide P2 together with other effective ingredients.

The present invention also includes an inhibitor with the activity of inhibiting EV71, which is obtained by using different cell-penetrating sequence, by modifying the sequence of or by using unnatural amino acids in polypeptide P2.

Enterovirus 3A protein is a high-efficiency ERSP which can bind to viral dsRNA to prevent it from being cut by Dicer, and thus inhibit the production of virus-derived vsiRNA, thereby avoiding the antiviral immunity of the host by RNAi pathway.

The polypeptide and the derivatives thereof according to the present invention are capable of inhibiting the function of enterovirus protein 3A, and may be an emerging therapeutic drug for EV71, which targets new targets and is of great significance for avoiding antiviral drug resistance.

Compared with the prior art, the present invention has the following advantages:

The P2 polypeptide and variants thereof have potent antiviral activity. This will provide a new strategy for the prevention and treatment of enterovirus, also provide a new theoretical basis for accelerating the development of anti-enterovirus polypeptide small molecule drugs. In addition, the clear antiviral mechanism of the P2 series polypeptides can ensure the safety for their application and the clarity for the optimization approach, which is convenient for further development in the future.

The polypeptides provided by the present invention are shown in Table 1.

| Peptide | SEQ ID NO: | Sequence | Tested | Antiviral (s) | $IC_{50}/EC_{50}$ | $CC_{50}$ |
|---|---|---|---|---|---|---|
| P1 | 6 | RRRRRRRRAISDLLAS | In vivo | EV71/CVA-16 | 7.038 µM | >100 µM |
| P2 | 2 | RRRRRRRREEVRQYCRDQ | in vitro | EV71/CVA-16 | 1.208 µM/ 1.533 µM | >100 µM |
| CR | 7 | YGRKKRRQRRRGSGCR | In vivo | EV71 | $IC_{50}/EC_{50}$ 1.7 µM | $CC_{50}$ |
| 3A-TAT-EP | 3 | YGRKKRRQRRRGSGEEVRQYCREQGWIIP | In vitro | EV71 | 4.36 µM | >100 µM |
| EP-PA | 8 | EEVRQYCREQGWIIP-βAK-C16 (palmitic acid (C16:0)) | In vitro | EV71 | 8.175 µM | / |
| EP-CHOL | 9 | EEVRQYCREQGWIIP-AK-cholesterol (Chol) | In vitro | EV71 | 11.35 µM | / |
| EP | 1 | EEVRQYCREQGWIIP | / | / | / | / |
| 3A-EP-DRI | 4 | Acetylated (Ac): Ac-piiwgqercyqrveepprrrqrrkkrgy-NH2 (all amino acids are D-amino acid) | In vitro | EV71 | 5.242 µM | >100 µM |
| 3A-EP-PEG4-PA | 5 | EEVRQYCREQGWIIP-AK-Polyethylene glycol 4 (PEG4)-K-C16 | In vitro | EV71 | 4.912 µM | >100 µM |
| ER | 10 | YGRKKRRQRRRGSGEEVRQYCR | In vitro | EV71/CVA-16 | 1.26 µM/ 3.211 µM | 290 µM |
| ER-DRI | 11 | Acetylated (Ac): Ac-rcyqrveepprrrqrrkkrgy-NH2 (all amino acids are D-amino acid) | In vivo | EV71/CVA-16/CVA-6/CVA-8 | 0.64 µM/ 0.856 µM | 117 µM |
| BP-8 | 12 | YGRKKRRQRRRGSGEAVREYCK | In vitro | CVB5/CVB3 | 1.1 µM/ 3.2 µM | >200 µM |
| BP-10 | 13 | YGRKKRRQRRRGSGEAVREYCKEK | In vitro | CVB5 | 1.5 µM/ | >200 µM |
| BP-15 | 14 | YGRKKRRQRRRGSGEAVREYCKEKGWLVP | In vitro | CVB5 | 6.25 µM/ | >100 µM |

In the present invention, polypeptides RRRRRRRR (R8) and YGRKKRRQRRR (TAT) are penetrating peptides, GSG is a peptide linker, and the amino acid sequences without the penetrating peptide and the peptide linker are the core sequences. In each example of the present invention, a negative control polypeptide is provided to show that the core sequences of the polypeptides in the present invention have good antiviral effects.

The materials and reagents used in the present invention are commercially available.

The present invention will be further explained below in conjunction with examples.

Example 1

Detection of Membrane Penetration Efficiency of Polypeptide P2

1. Material:

MEM medium (Thermo), serum (Gibco), immunofluorescence plate (NEST), PBS, DAPI, and paraformaldehyde were purchased in the market.

Polypeptide P2 was synthesized by Nanjing GenScript Company, and its sequence is shown in SEQ ID NO: 2.

2. Experimental Procedure

The experiment was performed in two groups in order to observe whether the addition of EV71 virus affect the entry of polypeptides into cells. In one group, EV71 virus and then polypeptide P2 were added, and in the other group, only the polypeptide was added. Negative control was set in each group.

Immunofluorescence experiment was performed as follows.

(1) 1 ml of RD cells in a special dish for immunofluorescence were treated and then collected at 30% confluence.

(2) The medium in the dish was aspirated, and the dish was washed three times (5 minutes for each wash) with 1 ml of 0.01 mol/L PBS (pH 7.4) to remove residual medium.

(3) 4% paraformaldehyde solution was prepared by dissolving 4 g paraformaldehyde solid in 100 ml PBS. Then 1 ml of the prepared 4% paraformaldehyde solution was added to each dish and incubated for 5 minutes to fix the cells.

(4) The 4% paraformaldehyde solution was aspirated, and the dish was washed three times (5 minutes for each wash) with 1 ml of 0.01 mol/L PBS (pH 7.4) to remove residual paraformaldehyde.

(5) 1 mg/ml DAPI solution was diluted with PBS to 100 ng/ml, and the diluted DAPI solution was added to the dish and incubated for 15 minutes.

(6) The solution was aspirated, and the dish was washed three times (5 minutes for each wash) with 1 ml of 0.01 mol/L PBS (pH 7.4) to remove residual solution.

(7) The dish was observed under a fluorescence microscope.

Polypeptides were labeled with fluorescence and tested for their membrane penetration efficiency in RD cells. Two groups of experiments were performed. One group was control group without virus infection, in which R8 and P2 were added respectively; the other group was EV71 infection group, in which cells were infected with EV71 and then R8 and P2 were added respectively. The two groups of experiment were carried out at the same time, with virus MOI=0.1, and a polypeptide concentration of 1 μM. The cells were fixed 12 h after the addition of the polypeptide, immunofluorescence experiments were performed, and the nuclei were stained with DAPI. The results show that the polypeptides can enter cells infected with or without virus, showing a good ability to penetrate cell membranes.

Figure 1B:
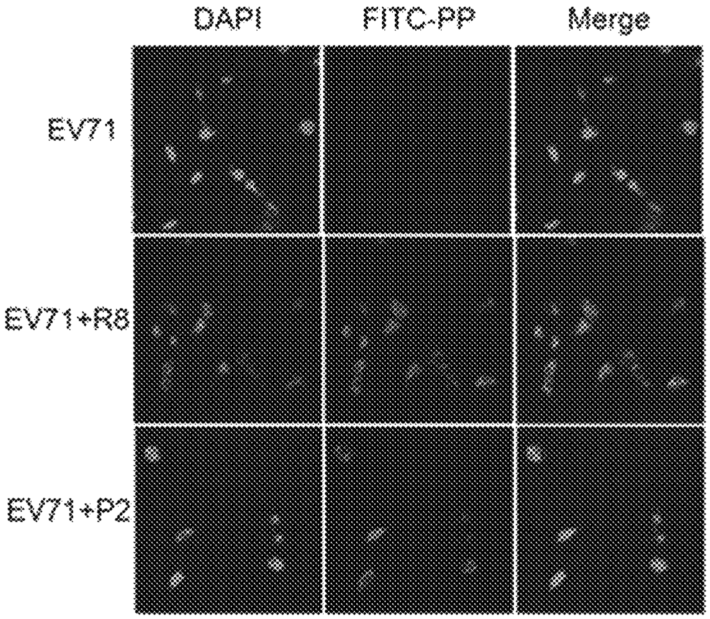

As shown in FIGS. 1A-1B, with or without virus, the polypeptides can be observed in both cells infected with or without virus, indicating that polypeptide P2 has a good ability to penetrate cell membrane.

Example 2

Detection of Cytotoxicity of Polypeptide P2

1. Experimental Materials

CCK-8 reagent was from MCE.

2. Experimental Procedure

Polypeptide P2 was desired to be able to inhibit viruses, and also to be non-toxic to cells. Therefore, the cytotoxicity test was used for detection, and untreated cells were used as the control group.

The experiment was performed as follows.

(1) RD cells were plated in a 96-well plate at 100 μl per well.

(2) After the cells reached 70%-80% confluence, the MEM medium containing 10% serum was replaced with a MEM medium containing 2% serum. Then, polypeptide P2 was added to generate gradient concentrations of 0.01 μM, 0.1 μM, 1 μM, 10 μM, and 100 μM (final concentration), respectively.

(3) The test was performed 24 hours after the addition of the polypeptide, and 10 μl of viable cell detection reagent CCK-8 was added to each well and mixed well.

(4) The plate was incubated at 37° C. for 2 h.

(5) The absorbance value at $OD_{450}$ was measured with a microplate reader.

Figure 2:
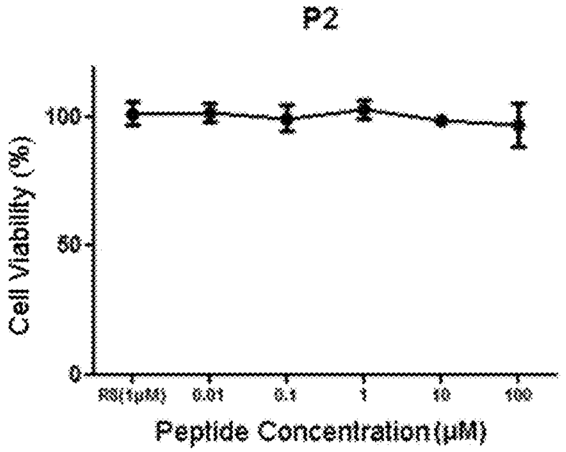
FIG. 2 shows the result of detecting the cytotoxicity of polypeptide P2 by CCK-8.

The results are shown in FIG. 2 and Table 2. Taking the cell viability of untreated group as 100%, there is no significant difference between the cell viability of the cells added with 100 μM polypeptide and that of the control group (untreated cells), which indicates that polypeptide P2 used in this study is not toxic to cells within 100 μM.

TABLE 2

| Concentration of polypeptide P2 (μM) | Cell viability (%) | | | Significance analysis (vs. without treatment) |
|---|---|---|---|---|
| R8 | 104.243900 | 103.446800 | 96.068770 | P = 0.4378 |
| 0 | 98.040830 | 104.606000 | 102.740100 | / |
| 0.01 | 98.040830 | 104.606000 | 102.740100 | P = 0.5000 |
| 0.1 | 94.404550 | 103.995900 | 100.622500 | P = 0.2844 |
| 1 | 105.193200 | 105.370600 | 98.812520 | P = 0.3357 |
| 10 | 96.602830 | 101.132500 | 99.031580 | P = 0.1444 |
| 100 | 90.146030 | 106.773400 | 94.068210 | P = 0.2116 |

Example 3

Detection of Antiviral Efficiency of Polypeptide

1. Materials

Total RNA extraction kit (Omega), 24-well plate, 100 mm dish, and 50 ml syringe, 0.22 μm filter membrane (Millipore), one step qRT-PCR kit (Takara) were purchased in the market. The water used in the RNA extraction and qRT-PCR was DEPC-treated water, and the entire experiment was carried out in an RNase free environment.

2. Amplification Virus (1) RD cells were plated in five 100 mm dishes.

(2) After the cells reached 70%-80% confluence, the MEM medium containing 10% serum was replaced with a MEM medium containing 2% serum. Then, 1 μl EV71 virus, CVA16 virus, CVB3 virus, or CVB5 virus at 10^7 PFU/ml were added, respectively.

(3) After 2 days, the cells were observed to see if the cytopathic effect (CPE) phenomenon occurred. When the changes were obvious, samples were collected as follows.
(4) The supernatant in the 100 mm dish was transferred into a 15 ml centrifuge tube, and centrifuged at 500 g for 5 min.
(5) The supernatant was transferred into a new 15 ml centrifuge tube, and filtered through 0.22 μm filter membrane with a 50 ml syringe.
(6) RNA was extracted from 100 μl of the supernatant obtained in step (5) and subjected to one step qRT-PCR to measure the virus titer, and the previously extracted virus RNA with known titer was handled together as a control.

3. Measure Antiviral Efficiency of Polypeptide in RD Cells.
(1) Different cells were plated in 24-well cell plates.
(2) After the cells reached 70%-80% confluence, the MEM medium containing 10% serum was replaced with a MEM medium containing 2% serum (0.5 ml/well), and 5 μl of 10^6 PFU/mL EV71 viruses per well were added.
(3) After 1 h, different polypeptides were added at a final concentration of 0.01 μM, 0.1 μM, 1 μM, 10 μM, and 50 μM, respectively.
(4) Samples were collected 24 hours after virus infection, and RNA was extracted with total RNA extraction kit as follows.
(5) The supernatant in the wells was discarded, then 350 μl of TRK Lysis Buffer was added to each well and the plate was shaken on the shaker for 5 minutes.
(6) 350 μl of 70% ethanol (DEPC-treated) was added to the well and the plate was shaken on the shaker for 5 minutes.
(7) The mixture in the well was transferred to a RNA extraction column and centrifuged at 12,000 g for 1 min.
(8) The solution collected in the recovery tube was added back to the column and centrifuged at 12,000 g for 1 min.
(9) RNA washing buffer 1 was added to the column and centrifuged at 12,000 g for 30 s.
(10) RNA washing buffer 2 was added to the column and centrifuged at 12,000 g for 1 min.
(11) Step (10) was repeated once.
(12) The column was centrifuged at 12000 g for 2 min to completely remove residual RNA washing buffer.
(13) 50 μl DEPC-treated $H_2O$ was added to the column and centrifuge at 12,000 g for 2 min.
(14) 2 μl RNA sample was used according to one step qRT-PCR kit for fluorescence quantification experiment.

RD cells added with R8 penetrating peptide (sequence: RRRRRRRR) were used as a negative control.

Figure 3:
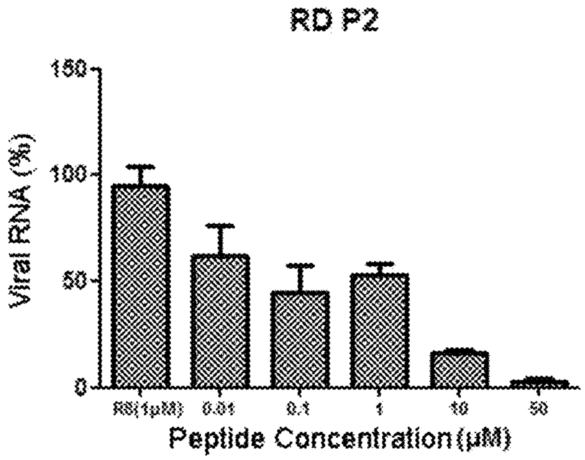
FIG. 3 shows the results of detecting the antiviral efficacy of polypeptide P2 in RD cells.

The results are shown in FIG. 3 and Table 3. The amount of viral RNA in the experimental group added with R8 and infected with EV71 virus was set as 100%. After the addition of polypeptide P2, the amount of virus decreased with the increase of the peptide concentration, and when the peptide concentration is 50 μM, the amount of virus is reduced to about 4%, demonstrating that polypeptide P2 has a good antiviral effect. The virus titer was detected by qRT-PCR, and the $IC_{50}$ value of P2 was 6.372 μM. As seen in FIG. 2, polypeptide P2 has no cytotoxicity within 100 μM. Therefore, it is shown that the polypeptide has a good antiviral effect and it is safe.

TABLE 3

| Results of 3 experiments | | | |
|---|---|---|---|
| Concentration of polypeptide (μM) | Relative Percentage of viral RNA (%) | | |
| 0.01 | 85.112880 | 75.771370 | 106.099300 |
| 0.1 | 77.353810 | 74.103940 | 77.353810 |
| 1 | 46.972400 | 46.319070 | 78.617520 |
| 10 | 17.463790 | 22.758900 | 20.427540 |
| 50 | 2.891023 | 2.288333 | 10.245860 |

RD cells were used to test the antiviral effect of polypeptide P2. EV71 (MOI=0.1) was added to RD cells at 80% confluence. After 1 hour of infection, polypeptide P2 was added at concentrations of 0.01 μM, 0.1 μM, 1 μM, 10 μM, and 50 μM, respectively. The samples were collected 24 hours later, and the total RNA was extracted. The level of viral genomic RNA was detected by qRT-PCR. The cells infected with the same type virus and added with penetrating peptide R8 were used as a control group. The results showed that with the increase of the polypeptide concentration, the viral RNA level decreased significantly, demonstrating that polypeptide P2 has obvious anti-EV71 activity.

Example 4

Test Antiviral Efficiency of Polypeptide P2 in Various Cells

1. Materials

HEK293T, Vero, and Huh7.5 cells

2. Determination of Antiviral Efficiency of Polypeptide P2 in Various Cells
(1) 293T cells, Vero cells and Huh7.5 cells were plated in 24-well plates respectively.
(2) After the cells reached 70%-80% confluence, the MEM medium containing 10% serum was replaced with a MEM medium containing 2% serum (0.5 ml/well), and 5 μl of 10^6 PFU/mL EV71 virus per well was added.
(3) After 1 h, polypeptide P2 was added to different cells at a final concentration of 0.01 μM, 0.1 μM, 1 μM, 10 μM, and 50 μM, respectively.
(4) Samples were collected 24 hours after virus infection, and RNA was extracted with a total RNA extraction kit as follows.
(5) The supernatant in each well was discarded, then 350 μl of TRK Lysis Buffer was added to the well and the plate was shaken on the shaker for 5 minutes.
(6) 350 μl of 70% ethanol (DEPC-treated) was added to the well and the plate was shaken on the shaker for 5 minutes.
(7) The mixture in the well was transferred to a RNA extraction column and centrifuged at 12,000 g for 1 min.
(8) The solution collected in the recovery tube was added back to the column and centrifuged at 12,000 g for 1 min.
(9) RNA washing buffer 1 was added to the column and centrifuged at 12,000 g for 30 s.
(10) RNA washing buffer 2 was added to the column and centrifuged at 12,000 g for 1 min.
(11) Step (10) was repeated once.
(12) The empty column was centrifuged at 12,000 g for 2 min to completely remove residual RNA washing buffer.
(13) 50 μl DEPC-treated $H_2O$ was added to the column and centrifuge at 12,000 g for 2 min.

(14) 2 μl RNA sample was used according to one step qRT-PCR kit for fluorescence quantification experiment.

Figure 4A:
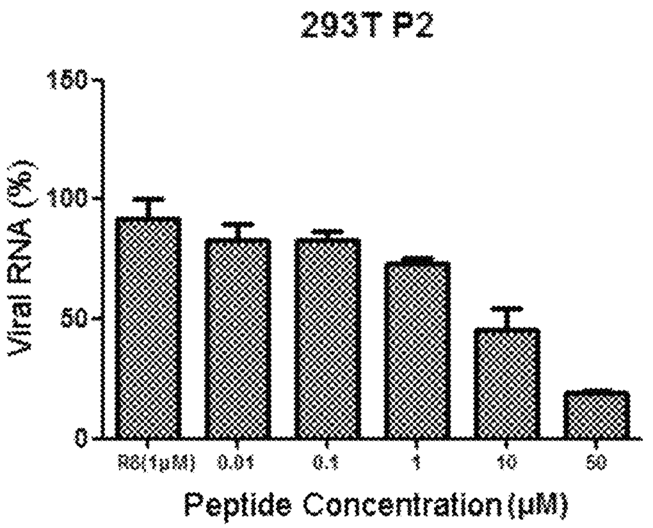
FIGS. 4A-4C show the results of detecting the antiviral efficacy of polypeptide P2 in various cells.
Figure 4B:
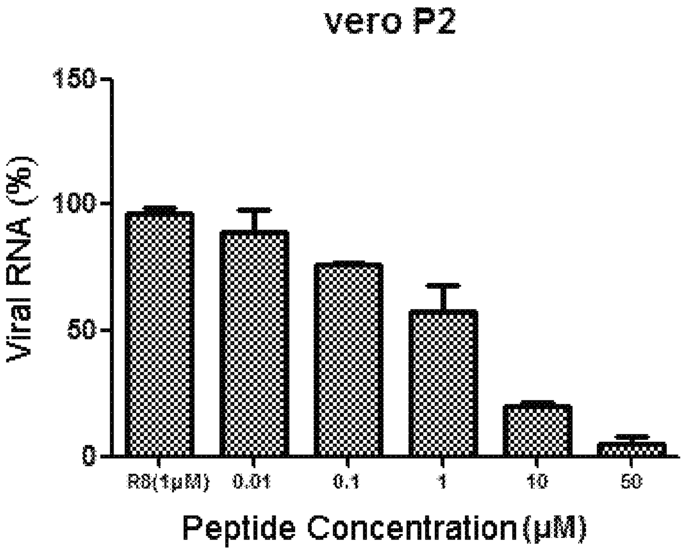
Figure 4C:
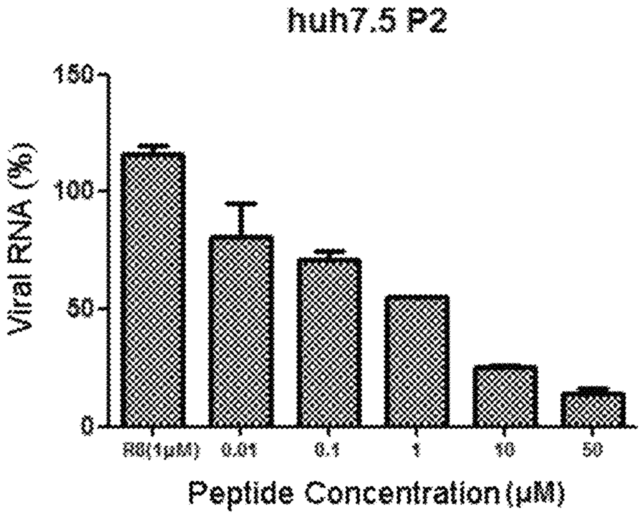

It can be seen in FIGS. 4A-4C that whether in RD cells, 293T cells, Vero cells or huh7.5 cells, polypeptide P2 can play a significant antiviral effect.

The $IC_{50}$ values measured in 293T cells, Vero cells and Huh7.5 cells were 9.677 μM, 1.958 μM and 1.842 μM, respectively.

Example 5 Test Antiviral Efficiency of Polypeptide P2 Variants

1. Materials

Polypeptides 3A-TAT-EP (shown in SEQ ID NO: 3), 3A-EP-DRI (shown in SEQ ID NO: 4) and 3A-EP-PEG4-PA (shown in SEQ ID NO: 5) were used and were all synthesized by company.

2. Determination of Antiviral Efficiency of the Variants of Polypeptide P2

(1) 293T cells were plated in a 24-well cell plate.

(2) After the cells reached 70%-80% confluence, the MEM medium containing 10% serum was replaced with a MEM medium containing 2% serum (0.5 ml/well), and 5 μl of 10^6 PFU/mL EV71 virus per well was added.

(3) After 1 hour, polypeptides P2, 3A-TAT-EP, 3A-EP-DRI and 3A-EP-PEG-PA were added at a final concentration of 0.01 μM, 0.1 μM, 1 μM, and 10 μM, respectively.

(4) Samples were collected 24 hours after virus infection, and RNA was extracted with a total RNA extraction kit.

(5) The supernatant in each well was discarded, then 350 μl of TRK Lysis Buffer was added to the well and the plate was shaken on the shaker for 5 minutes.

(6) 350 μl of 70% ethanol (DEPC-treated) was added to the well and the plate was shaken on the shaker for 5 minutes.

(7) The mixture in the well was transferred to a RNA extraction column and centrifuged at 12000 g for 1 min.

(8) The solution collected in the recovery tube was added back to the column and centrifuged at 12,000 g for 1 min.

(9) RNA washing buffer 1 was added to the column and centrifuged at 12,000 g for 30 s.

(10) RNA washing buffer 2 was added to the column and centrifuged at 12,000 g for 1 min.

(11) Step (10) was repeated once.

(12) The empty column was centrifuged at 12,000 g for 2 min to completely remove residual RNA washing buffer.

(13) 50 μl DEPC-treated water was added to the column and centrifuge at 12000 g for 2 min.

(14) 2 μl RNA sample was used according to one step qRT-PCR kit for fluorescence quantification experiment.

3. Detection of Virus Inhibitory Activity of 3A-TAT-EP and 3A-EP-DRI in RD Cells by CCK8 Method (1) RD cells in good growth state were plated in a 96-well plate at $1\times10^4$ cells per well and cultured in 5% $CO_2$ at 37° C. for 24 h.

(2) polypeptides (3A-TAT-EP, 3A-EP-DRI) were diluted in 2-fold series with MEM containing 2% FBS to obtain 40 μM, 20 μM, 10 μM, 5 μM, 2.5 μM, 1.25 μM, 0.625 μM, 0.313 μM concentrations at a final volume of 100 μl in a new 96-well plate. Each concentration was tested in triplicate.

(3) The diluted virus solution was added to the plate of step (1), 100 μL per well with the final virus concentration was 0.1 MOI. Wells without polypeptide and virus (well without treatment), wells with virus only were used as controls.

(4) The mixture of step (2) was added to the 96-well plate plated with cells in step (1) and incubated in 5% $CO_2$ at 37° C. for 24 h. Then CCK8 kit was used to determine the inhibitory effect of the polypeptide on virus.

(5) The inhibition rate of different concentrations of polypeptides on viral infection was calculated using the following formula:

OD means the value of $OD_{450}$-$OD_{630}$, inhibition rate=(OD well with treatment−OD well with virus only)×100%/(OD well without treatment−OD well with virus only)

Figure 5:
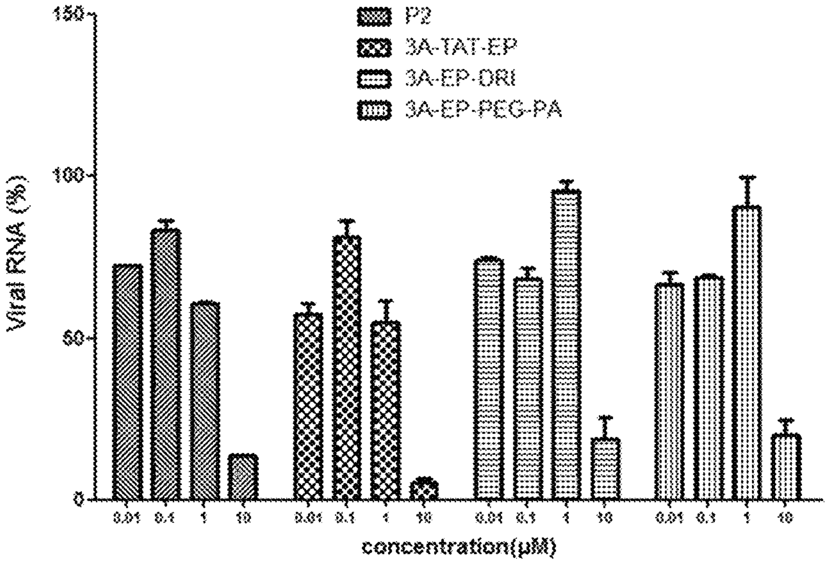
FIG. 5 shows the results of detecting the antiviral efficacy of the variants of polypeptide P2.

The results are shown in FIG. 5. It is shown than the polypeptide P2 variants 3A-TAT-EP (shown in SEQ ID NO: 3), 3A-EP-DRI (shown in SEQ ID NO: 4) and 3A-EP-PEG4-PA (shown in SEQ ID NO: 5) can also be used as an EV71 inhibitor, and have improved antiviral effect. The $IC_{50}$ of 3A-EP-PEG4-PA measured by qRT-PCR is 3.25 μM.

Figure 6:
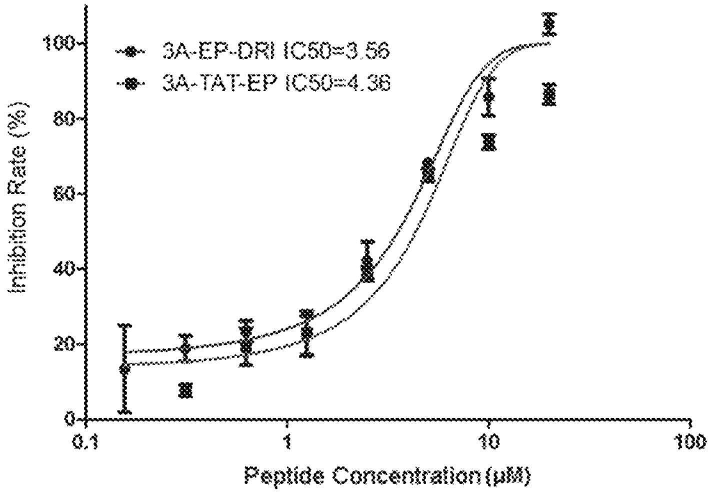
FIG. 6 shows the results of detecting the antiviral efficacy of polypeptides 3A-EP-DRI and 3A-TAT-EP.

In FIG. 6, the determination of the viral inhibitory activity of the polypeptides by the CCK8 method shows that the $IC_{50}$ of 3A-TAT-EP is 4.36 μM, and the $IC_{50}$ of 3A-EP-DRI is 3.56 μM.

Example 6

Detection of Membrane Penetration Efficiency of Polypeptide P1

1. Material:

MEM medium (Thermo), serum (Gibco), immunofluorescence plate (NEST), PBS, DAPI, and paraformaldehyde were purchased from markets.

Polypeptide P1 was synthesized by Nanjing GenScript Company, and its sequence is shown in SEQ ID NO: 6.

2. Experimental Procedure

The experiment was performed in two groups in order to observe whether the addition of EV71 virus affects the entry of polypeptides into cells. In one group, EV71 virus and then polypeptide P2 were added, and in the other group, only the polypeptide was added. Negative control was set in each group.

Immunofluorescence experiment was performed as follows.

(1) 1 ml of RD cells in a special dish for immunofluorescence were treated and then collected at 30% confluence.

(2) The medium in the dish was aspirated, and the dish was washed three times (5 minutes for each wash) with 1 ml of 0.01 mol/L PBS (pH 7.4) to remove residual medium.

(3) 4% paraformaldehyde solution was prepared by dissolving 4 g paraformaldehyde solid in 100 ml PBS. Then 1 ml of the prepared 4% paraformaldehyde solution was added to each dish and incubated for 5 minutes to fix the cells.

(4) The 4% paraformaldehyde solution was aspirated, and the dish was washed three times (5 minutes for each wash) with 1 ml of 0.01 mol/L PBS (pH 7.4) to remove residual paraformaldehyde.

(5) 1 mg/ml DAPI solution was diluted with PBS to 100 ng/ml, and the diluted DAPI solution was added to the dish and incubated for 15 minutes.

(6) The solution was aspirated, and the dish was washed three times (5 minutes for each wash) with 1 ml of 0.01 mol/L PBS (pH 7.4) to remove residual solution.

(7) The dish was observed under a fluorescence microscope.

Polypeptides were labeled with fluorescence and tested for their membrane penetration efficiency in RD cells. Two groups of experiment were performed. One group was control group without virus infection, in which blank, R8, P1 and P2 were added respectively; the other group was EV71 infection group, in which cells were infected with EV71 and then blank, R8, P1 and P2 were added respectively. The two groups of experiment were carried out at the same time, with virus MOI=0.1, and a polypeptide concentration of 1 μM. The cells were fixed 12 h after the addition of the polypeptide, immunofluorescence experiments were performed, and the nuclei were stained with DAPI. The results show that the polypeptides can enter cells infected with or without virus, showing a good ability to penetrate cell membranes.

Figure 14:
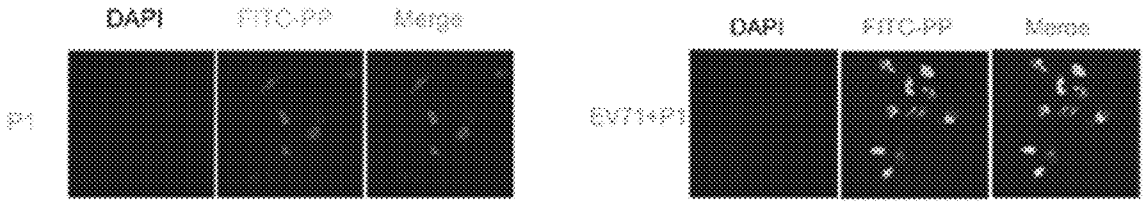
FIG. 14 shows the results of detecting the membrane penetration efficiency of polypeptide P1 in RD cells.

As shown in FIG. 14, the polypeptides can be observed in both cells infected with or without virus, indicating that polypeptide P1 has a good ability to penetrate cell membrane.

Example 7

Determination of Cytotoxicity of Polypeptide P1

1. Experimental Materials

CCK-8 reagent was from MCE.

2. Experimental Procedure

Polypeptide P1 was desired to be able to inhibit viruses, also to be non-toxic to cells. Therefore, the cytotoxicity test was used for detection, and untreated cells were used as the control group.

The experiment was performed as follows.

(1) RD cells were plated in a 96-well plate at 100 μl per well.

(2) After the cells reached 70%-80% confluence, the MEM medium containing 10% serum was replaced with a MEM medium containing 2% serum. Then, polypeptide P1 was added to generate gradient concentrations of 0.01 μM, 0.1 μM, 1 μM, 10 μM, and 100 μM (final concentrations), respectively.

(3) The test was performed 24 hours after the addition of the polypeptide, and 10 μl of viable cell detection reagent CCK-8 was added to each well and mixed well.

(4) The plate was incubated at 37° C. for 2 h.

(5) The absorbance value at $OD_{450}$ was measured with a microplate reader.

Figure 15:
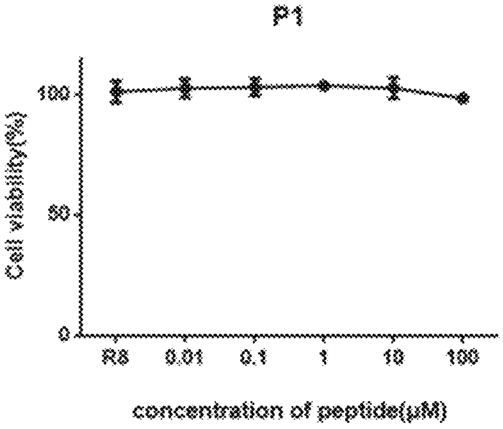
FIG. 15 shows the results of cytotoxicity experiments of polypeptide P1.

The results are shown in FIG. 15 and Table 4. Taking the cell viability of untreated group as 100%, there is no significant difference between the cell viability of the cells added with 100 μM polypeptide and that of the control group (untreated cells), which indicates that polypeptide P1 used in this study is not toxic to cells within 100 μM.

TABLE 4

| Concentration of polypeptide (μM) | Cell viability (%) | | | Significance analysis (vs. 0 μM group) |
|---|---|---|---|---|
| 0 | 104.243900 | 103.446800 | 96.068770 | |
| 0.01 | 102.884300 | 98.822470 | 106.317300 | P = 0.3481 |
| 0.1 | 105.509100 | 104.853800 | 99.136560 | P = 0.2964 |
| 1 | 102.718800 | 105.463300 | 102.899100 | P = 0.2124 |
| 10 | 102.687200 | 107.144700 | 98.611670 | P = 0.3428 |
| 100 | 100.233100 | 97.060650 | 98.376590 | P = 0.1920 |

RD cells were used to test the antiviral effect of polypeptide P1. When RD cells reached 80% confluence, polypeptide P1 was added at concentrations of 0 μM (control group), 0.01 μM, 0.1 μM, 1 μM, 10 μM, and 100 μM, respectively. Three parallel wells were used for each concentration. The test was carried out 24 hours later, and the cell viability was detected using the CCK-8 kit. The results showed that there was no significant difference in the cell survival rate between the group added with 100 μM polypeptide P1 and the control group, indicating that polypeptide P1 is not toxic to cells within 100 μM.

Example 8

Determination of Cytotoxicity of Polypeptide 3A-TAT-EP

1. Experimental Materials

CCK-8 reagent was from MCE.

2. Experimental Procedure

Polypeptide 3A-TAT-EP was desired to be able to inhibit viruses, and also to be non-toxic to cells. Therefore, the cytotoxicity test was used for detection, and untreated cells were used as the control group.

The experiment was performed as follows.

(1) RD cells were plated in a 96-well plate at 100 μl per well.

(2) After the cells reached 70%-80% confluence, the MEM medium containing 10% serum was replaced with a MEM medium containing 2% serum. Then, polypeptide 3A-TAT-EP was added to generate gradient concentrations of 0.01 μM, 0.1 μM, 1 μM, 10 μM, and 100 μM (final concentrations), respectively.

(3) The test was performed 24 hours after the addition of the polypeptide, and 10 μl of viable cell detection reagent CCK-8 was added to each well and mixed well.

(4) The plate was incubated at 37° C. for 2 h.

(5) The absorbance value at $OD_{450}$ was measured with a microplate reader.

Figure 16:
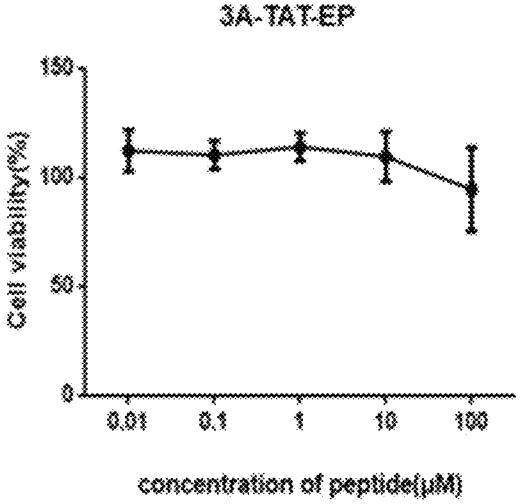
FIG. 16 shows the results of cytotoxicity experiments of polypeptide 3A-TAT-EP.

The results are shown in FIG. 16 and Table 5. Taking the cell viability of untreated group as 100%, there is no significant difference between the cell viability of the cells added with 100 μM polypeptide and that of the control group (untreated cells), which indicates that polypeptide 3A-TAT-EP used in this study is not toxic to cells within 100 μM.

TABLE 5

| Concentration of polypeptide (μM) | Cell viability (%) | | | Significance analysis (vs. 0 μM group) |
|---|---|---|---|---|
| 0 | 104.243900 | 103.446800 | 96.068770 | |
| 0.01 | 102.884300 | 98.822470 | 106.317300 | P = 0.3481 |
| 0.1 | 105.509100 | 104.853800 | 99.136560 | P = 0.2964 |
| 1 | 102.718800 | 105.463300 | 102.899100 | P = 0.2124 |
| 10 | 102.687200 | 107.144700 | 98.611670 | P = 0.3428 |
| 100 | 100.233100 | 97.060650 | 98.376590 | P = 0.1920 |

RD cells were used to test the antiviral effect of polypeptide 3A-TAT-EP. When RD cells reached 80% confluence, polypeptide 3A-TAT-EP was added at concentrations of 0

μM (control group), 0.01 μM, 0.1 μM, 1 μM, 10 μM, and 100 μM, respectively. Three parallel wells were used for each concentration. The test was carried out 24 hours later, and the cell viability was detected using the CCK-8 kit. The results showed that there was no significant difference in the cell survival rate between the group added with 100 μM polypeptide 3A-TAT-EP and the control group, indicating that polypeptide P1 is not toxic to cells within 100 μM.

Example 9

Determination of Cytotoxicity of Polypeptides 3A-EP-DRI and 3A-EP-PEG4-PA

1. Experimental Materials

CCK-8 reagent was from MCE.

2. Experimental Procedure

Polypeptides 3A-EP-DRI and 3A-EP-PEG4-PA were desired to be able to inhibit viruses, and also to be non-toxic to cells. Therefore, the cytotoxicity test was used for detection, and untreated cells were used as the control group.

The experiment was performed as follows.

(1) RD cells were plated in a 96-well plate at 100 μl per well.

(2) After the cells reached 70%-80% confluence, the MEM medium containing 10% serum was replaced with a MEM medium containing 2% serum. Then, 3A-EP-DRI or 3A-EP-PEG4-PA was added to generate gradient concentrations of 0.01 μM, 0.1 μM, 1 μM, 10 μM, and 50 μM (final concentrations), respectively.

(3) The test was performed 24 hours after the addition of the polypeptide, and 10 μl of viable cell detection reagent CCK-8 was added to each well and mixed well.

(4) The plate was incubated at 37° C. for 2 h.

(5) The absorbance value at $OD_{450}$ was measured with a microplate reader.

Figure 17:
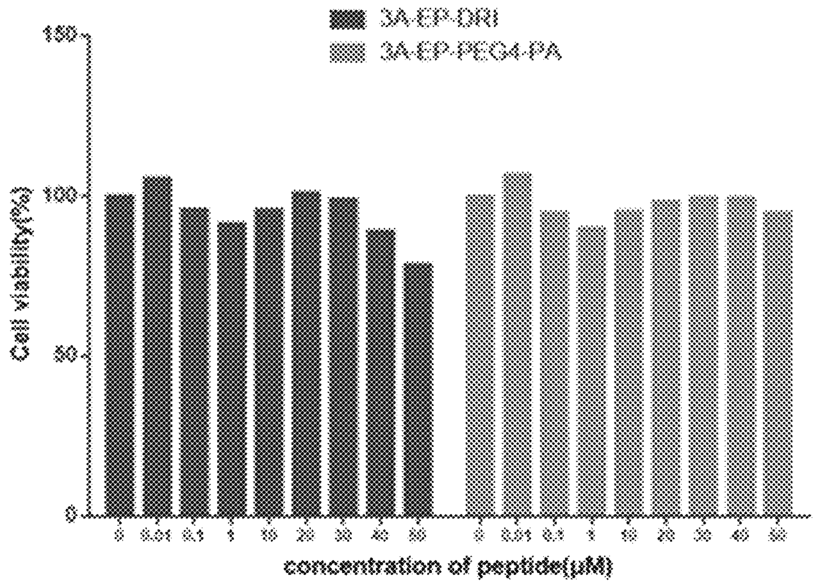
FIG. 17 shows the results of cytotoxicity experiments of polypeptides 3A-EP-DRI and 3A-EP-PEG4-PA.

The results are shown in FIG. 17 and Table 6. Taking the cell viability of untreated group as 100%, there is no significant difference between the cell viability of the cells added with 50 μM polypeptide and that of the control group (untreated cells), which indicates that polypeptides 3A-EP-DRI and 3A-EP-PEG4-PA used in this study are not toxic to cells within 50 μM.

TABLE 6

| Concentration of polypeptide (μM) | Cell viability (%) 3A-EP-DRI | 3A-EP-PEG4-PA |
|---|---|---|
| 0.01 | 105.545100 | 106.594900 |
| 0.1 | 95.854640 | 94.885600 |
| 1 | 91.332440 | 89.878870 |
| 10 | 95.693140 | 95.289370 |
| 20 | 100.942100 | 98.358010 |
| 30 | 99.004040 | 99.488560 |
| 40 | 88.990580 | 99.327050 |
| 50 | 78.492600 | 94.804850 |

RD cells were used to test the antiviral effect of polypeptides 3A-EP-DRI and 3A-EP-PEG4-PA. When RD cells reached 80% confluence, polypeptide 3A-EP-DRI or 3A-EP-PEG4-PA was added at concentrations of 0 μM (control group), 0.01 μM, 0.1 μM, 1 μM, 10 μM, and 50 μM, respectively. Three parallel wells were used for each concentration. The test was carried out 24 hours later, and the cell viability was detected using the CCK-8 kit. The results showed that there was no significant difference in the cell survival rate between the group added with 50 μM polypeptide 3A-EP-DRI or 3A-EP-PEG4-PA and the control group, indicating that polypeptides 3A-EP-DRI and 3A-EP-PEG4-PA are not toxic to cells within 50 μM.

Example 10

Detection of Antiviral Efficiency of Polypeptide

1. Materials

Total RNA extraction kit (Omega), 24-well plate, 100 mm dish, and 50 ml syringe, 0.22 μm filter membrane (Millipore), one step qRT-PCR kit (Takara) were purchased in the market. The water used in the RNA extraction and qRT-PCR was DEPC-treated water, and the entire experiment was carried out in an RNase-free environment.

2. Amplification of Virus (1) RD cells were plated in five 100 mm dishes.

(2) After the cells reached 70%-80% confluence, the MEM medium containing 10% serum was replaced with a MEM medium containing 2% serum. Then, 1 μl EV71 virus at 10^7 PFU/ml was added, respectively.

(3) After 2 days, the cells were observed to see if the CPE phenomenon occurred. When the changes were obvious, samples were collected as follows.

(4) The supernatant in the 100 mm dish was transferred into a 15 ml centrifuge tube, and centrifuged at 500 g for 5 min.

(5) The supernatant was transferred into a new 15 ml centrifuge tube, and filtered through 0.22 μm filter membrane with a 50 ml syringe.

(6) RNA was extracted from 100 μl of the supernatant obtained in step (5) and subjected to one step qRT-PCR to measure the virus titer, and the previously extracted virus RNA with known titer was handled together as a control.

3. Measure Antiviral Efficiency of Polypeptide in RD Cells (1) Different cells were plated in 24-well cell plates.

(2) After the cells reached 70%-80% confluence, the MEM medium containing 10% serum was replaced with a MEM medium containing 2% serum (0.5 ml/well), and 5 μl of 10^6 PFU/mL EV71 virus per well were added.

(3) After 1 h, different polypeptides were added at a final concentration of 0.01 μM, 0.1 μM, 1 μM and 10 μM, respectively. Wells without treatment were used as control.

(4) Samples were collected 24 hours after virus infection, and RNA was extracted with total RNA extraction kit as follows.

(5) The supernatant in the wells was discarded, then 350 μl of TRK Lysis Buffer was added to each well and the plate was shaken on the shaker for 5 minutes.

(6) 350 μl of 70% ethanol (DEPC-treated) was added to the well and the plate was shaken on the shaker for 5 minutes.

(7) The mixture in the well was transferred to a RNA extraction column and centrifuged at 12000 g for 1 min.

(8) The solution collected in the recovery tube was added back to the column and centrifuged at 12,000 g for 1 min.

(9) RNA washing buffer 1 was added to the column and centrifuged at 12,000 g for 30 s.

(10) RNA washing buffer 2 was added to the column and centrifuged at 12,000 g for 1 min.

(11) Step (10) was repeated once.

(12) The column was centrifuged at 12,000 g for 2 min to completely remove residual RNA washing buffer.

(13) 50 μl DEPC-treated $H_2O$ was added to the column and centrifuge at 12,000 g for 2 min.

(14) 2 μl RNA sample was used according to one step qRT-PCR kit for fluorescence quantification experiment.

Figure 18:
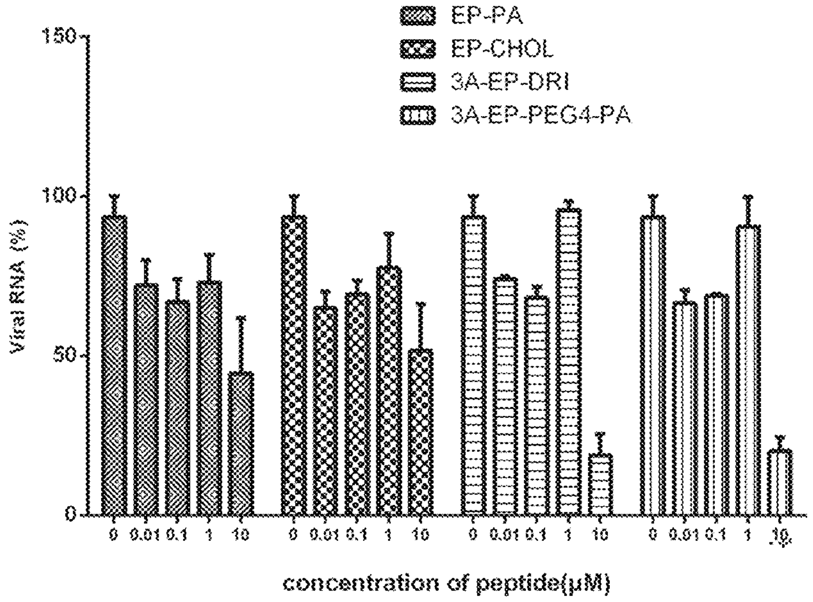
FIG. 18 shows the results of detecting the antiviral effects of polypeptides EP-PA, EP-CHOL, 3A-EP-DRI and 3A-EP-PEG4-PA.
Figure 19:
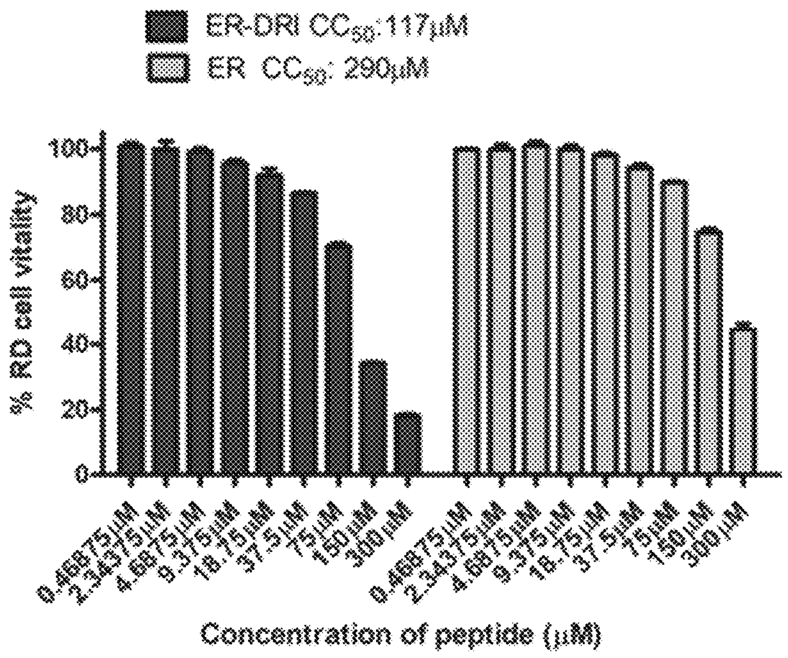
FIG. 19 shows the results of toxicity experiments of ER-DRI and ER in RD cells.

The test results of polypeptides EP-PA, EP-CHOL, 3A-EP-DRI and 3A-EP-PEG4-PA are shown in FIG. 18 and tables 7 to 10.

TABLE 7

| Concentration of polypeptide EP-PA (μM) | Relative viral RNA amount (%) | | | Significance analysis (vs. 0 μM group) |
|---|---|---|---|---|
| 0 | 100.569000 | 80.164300 | 99.430990 | / |
| 0.01 | 83.066650 | 76.474690 | 56.742880 | P = 0.0539 |
| 0.1 | 79.012950 | 67.554600 | 53.702980 | P = 0.0271 |
| 1 | 86.289260 | 75.980030 | 56.914250 | P = 0.0672 |
| 10 | 43.712254 | 61.850070 | 27.037620 | P = 0.0075 |

TABLE 8

| Concentration of polypeptide EP-CHOL (μM) | Relative viral RNA amount (%) | | | Significance analysis (vs. 0 μM group) |
|---|---|---|---|---|
| 0 | 100.569000 | 80.164300 | 99.430990 | / |
| 0.01 | 75.485760 | 59.539330 | 59.747630 | P = 0.0141 |
| 0.1 | 75.761750 | 70.988640 | 60.975830 | P = 0.0191 |
| 1 | 96.783520 | 76.068370 | 59.554410 | P = 0.1382 |
| 10 | 39.120456 | 66.179340 | 37.087750 | P = 0.0081 |

TABLE 9

| Concentration of polypeptide 3A-EP-DRI (μM) | Relative viral RNA amount (%) | | | Significance analysis (vs. 0 μM group) |
|---|---|---|---|---|
| 0 | 100.569000 | 80.164300 | 99.430990 | / |
| 0.01 | 75.931920 | 73.357810 | 72.892740 | P = 0.0222 |
| 0.1 | 72.523670 | 70.587060 | 61.379300 | P = 0.0139 |
| 1 | 100.475300 | 95.841450 | 90.712620 | P = 0.3832 |
| 10 | 29.812460 | 19.585250 | 7.211936 | P = 0.0007 |

TABLE 10

| Concentration of polypeptide 3A-EP-PEG4-PA (μM) | Relative viral RNA amount (%) | | | Significance analysis (vs. 0 μM group) |
|---|---|---|---|---|
| 0 | 100.569000 | 80.164300 | 99.430990 | / |
| 0.01 | 72.500240 | 68.123620 | 59.095570 | P = 0.0127 |
| 0.1 | 69.964290 | 68.685590 | 67.809440 | P = 0.0105 |
| 1 | 107.086800 | 89.256320 | 75.236370 | P = 0.4607 |
| 10 | 24.576220 | 24.508320 | 11.301410 | P = 0.0004 |

RD cells were used to test the antiviral effect of polypeptides EP-PA, EP-CHOL, 3A-EP-DRI and 3A-EP-PEG4-PA. EV71 virus was added to RD cells at 80% confluence (MOI=0.1). After 1 hour of infection, polypeptides EP-PA, EP-CHOL, 3A-EP-DRI or 3A-EP-PEG4-PA was added at concentrations of 0.01 μM, 0.1 μM, 1 μM, and 10 μM, respectively. The samples were collected 24 hours later, and the total cell RNA was extracted. The level of viral genomic RNA was measured by qRT-PCR. The cells infected with virus but without polypeptide treatment were used as a control group. The results show that all polypeptides have anti-EV71 activity, and increasing the polypeptide concentration significantly inhibits the expression level of viral RNA.

Figure 22:
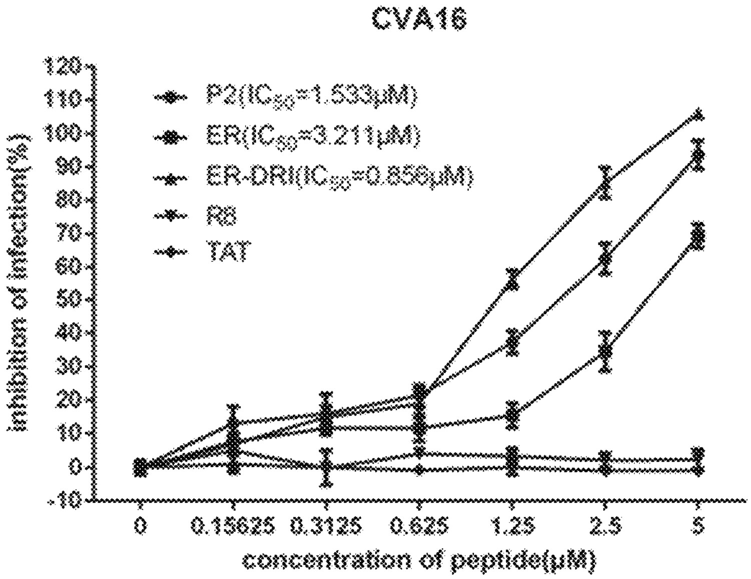
FIG. 22 shows the results of detecting the anti-CVA16 effects of polypeptides P2, ER, ER-DRI, R8 and TAT.

The results of anti-CVA16 virus effect of polypeptides P2, ER and ER-DRI are shown in FIG. 22 and tables 11-15.

TABLE 11

| Concentration of polypeptide P2 (μM) | Virus inhibition rate (%) | | |
|---|---|---|---|
| 0.15625 | 19.070900 | 16.870410 | 2.933985 |
| 0.3125 | 27.139360 | 12.836190 | 7.885086 |
| 0.625 | 24.388750 | 24.572130 | 15.220050 |
| 1.25 | 42.542790 | 30.990220 | 38.325180 |
| 2.5 | 71.149150 | 60.696820 | 55.745720 |
| 5 | 101.039100 | 86.552570 | 93.154040 |

TABLE 12

| Concentration of polypeptide ER (μM) | Virus inhibition rate (%) | | |
|---|---|---|---|
| 0.15625 | 11.002450 | 6.418093 | 5.134474 |
| 0.3125 | 8.618582 | 15.220050 | 11.002450 |
| 0.625 | 19.437650 | 6.784841 | 8.618582 |
| 1.25 | 15.953550 | 21.271390 | 8.985330 |
| 2.5 | 44.376530 | 24.755500 | 34.474330 |
| 5 | 71.699260 | 73.716380 | 62.530560 |

TABLE 13

| Concentration of polypeptide ER-DRI (μM) | Virus inhibition rate (%) | | |
|---|---|---|---|
| 0.15625 | 7.885086 | 3.667482 | 8.801956 |
| 0.3125 | 12.102690 | 11.185820 | 21.454770 |
| 0.625 | 15.770170 | 13.754320 | 27.139360 |
| 1.25 | 59.046460 | 58.863080 | 50.794620 |
| 2.5 | 93.520780 | 84.168700 | 77.933980 |
| 5 | 104.706600 | 107.273800 | 106.173600 |

TABLE 14

| Concentration of polypeptide R8 (μM) | Virus inhibition rate (%) | | |
|---|---|---|---|
| 0.15625 | −5.187778 | 10.914710 | 9.456473 |
| 0.3125 | −9.961808 | 7.600530 | 1.900133 |
| 0.625 | 0.5410566 | 6.009722 | 5.744587 |
| 1.25 | 5.612020 | −0.8911521 | 5.479452 |
| 2.5 | 4.949183 | −1.941439 | 3.500955 |
| 5 | −1.654997 | 0.8274984 | 7.733098 |

TABLE 15

| Concentration of polypeptide TAT (μM) | Virus inhibition rate (%) | | |
|---|---|---|---|
| 0.15625 | −3.004861 | 5.877154 | 0.1767565 |
| 0.3125 | 2.960672 | −0.8837826 | −2.076889 |

TABLE 15-continued

| Concentration of polypeptide TAT (μM) | Virus inhibition rate (%) | | |
|---|---|---|---|
| 0.625 | −3.946531 | 0.5744587 | 1.104728 |
| 1.25 | 4.021211 | −0.4860804 | −3.535130 |
| 2.5 | 1.237296 | −2.607159 | −1.654997 |
| 5 | −1.654997 | 1.782304 | −2.800764 |

RD cells were used to test the antiviral effect of polypeptides P2, ER and ER-DRI, and penetrating peptide R8 and TAT were used as controls. EV71 was added to RD cells at 80% confluence (MOI=0.1). After 1 hour of infection, polypeptides P2, ER, ER-DRI, R8 or TAT was added at concentrations of 0.15625 μM, 0.3125 μM, 0.625 μM, 1.25 μM, 2.5 μM, and 5 μM, respectively. The CCK-8 kit was used to test the inhibitory activity of the polypeptide against the virus 24 hours after infection. Inhibition rate of polypeptide=(OD well with treatment−OD well with virus only)×100%/(OD well without treatment−OD well with virus only), OD refers to the value of $OD_{450}$-$OD_{630}$. The results show that the peptides P2, ER, and ER-DRI can significantly inhibit CVA16, while the penetrating peptide R8 and TAT have no effect on the virus. The $IC_{50}$ of P2 is 1.533 μM, the $IC_{50}$ of ER is 3.211 μM, and the $IC_{50}$ of ER-DRI is 0.856 μM.

Example 11

Test Antiviral Activity of Polypeptide P1 against EV71 and CVA16 in Mice

1. Materials

P1 (sequence: RRRRRRRRAISDLLAS) was commercially synthesized. Newborn 2-day-old ICR suckling mice were used in the experiment.

2. Antiviral Activity of Polypeptide P1 in Mice (1) 8 2-day-old ICR mice were randomly divided into two groups, 4 in each group. The 8 mice were administered EV71 by intraperitoneal injection at a dose of $10^8$ PFU/ml.

(2) At the same time, one group was intraperitoneally injected with 10 mg/kg of polypeptide P1 as a treatment group, and the other group was intraperitoneally injected with an equal amount of PBS as a control group.

(3) Polypeptide and PBS were injected every 12 h for 5 days.

(4) At the fifth day, the mice were euthanized, and their hind limb muscle tissues were collected and triturated with Trizol (Invitrogen) to extract total RNA.

(5) Fluorescence quantification experiments were performed using a one step qRT-PCR kit.

Figure 7:
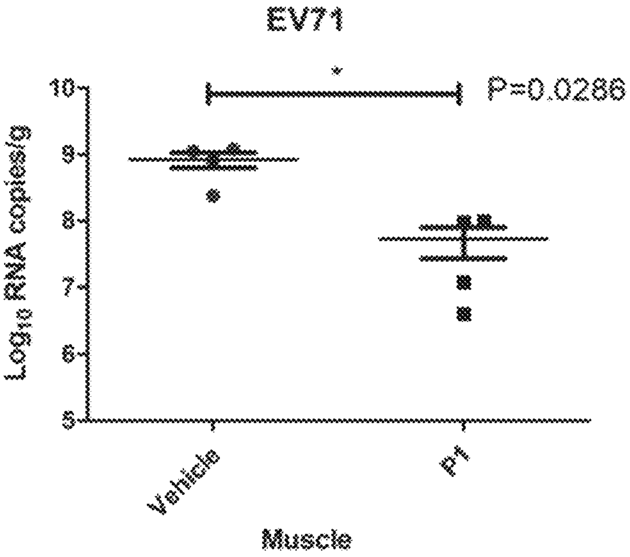
FIG. 7 shows the results of detecting the antiviral activity of polypeptide P1 against EV71 in mice.

The results are shown in FIG. 7 and Table 16. It can be seen that P1 can significantly reduce the EV71 viral load in mice.

3. The Procedure for Detecting the Antiviral Activity of P1 Against CVA16 in Mice is Similar as the EV71 Experiment.

Figure 8:
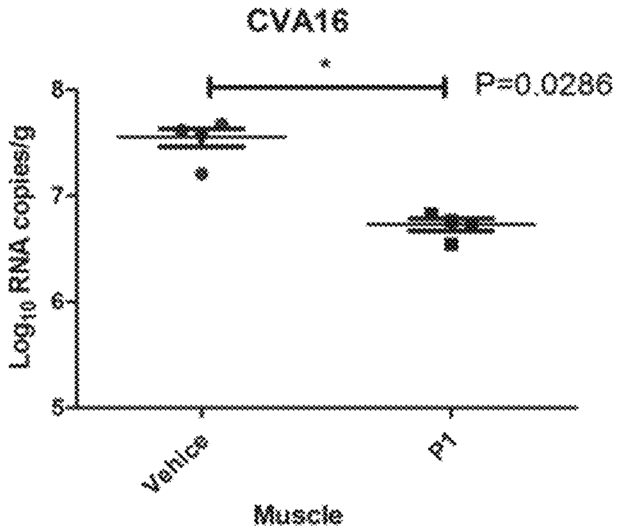
FIG. 8 shows the results of detecting the antiviral activity of polypeptide P1 against CVA16 in mice.

The results are shown in FIG. 8 and Table 17. It can be seen that P1 can significantly reduce the viral load of CVA16 in mice.

TABLE 16

| Sample | Number of EV71 virus copy in muscle tissue (Copies/g) | | | | Significance analysis (treatment vs. control) |
|---|---|---|---|---|---|
| PBS (control) | 1.206809e+009 | 1.122504e+009 | 8.221773e+008 | 2.381125e+008 | P = 0.0286 |
| P1 (treatment) | 9.934962e+007 | 9.702361e+007 | 4072066.000 | 1.202581e+007 | |

TABLE 17

| Sample | Number of CVA16 virus copys in muscle tissue (Copies/g) | | | | Significance analysis (treatment vs. control) |
|---|---|---|---|---|---|
| PBS (control) | 1.606804e+007 | 3.814315e+007 | 4.760443e+007 | 4.175508e+007 | P = 0.0286 |
| P1 (drug) | 3538852 | 5293714 | 5875037 | 6810972 | |

Example 12

Detection of Antiviral Activity of Polypeptide CR against EV71 in RD Cells (1) RD cells in good growth state were plated in a 96-well plate.

(2) After the cells reached 70%-80% confluence, the MEM medium containing 10% serum was replaced with a MEM medium containing 2% serum. Group without polypeptide and virus, and group with virus but without polypeptide were included as controls. The final virus concentration was 0.1 MOI.

(3) 1 h later, polypeptide CR at a final concentration of 5 μM, 2.5 μM, 1.25 μM, 0.625 μM, 0.3125 μM, and 0.15625 μM was added, respectively. Group without polypeptide and virus, and group with virus but without polypeptide were set as controls.

(4) 24 hours after virus infection, when the change in the control group with only virus was obvious, 10 μl of viable cell detection agent CCK-8 was added to each well and mixed well.

(5) The plate was incubated at 37° C. for 2 h.

(6) The absorbance value at $OD_{450}$ was measured with a microplate reader. Inhibition rate of polypeptide=(OD well with treatment−OD well with virus only)×100%/(OD well without treatment−OD well with virus only), OD refers to the value of $OD_{450}$-$OD_{630}$.

Figure 9:
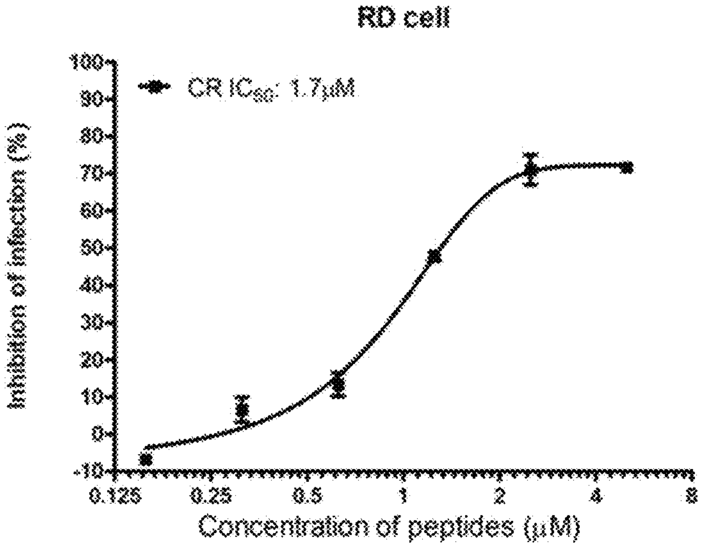
FIG. 9 shows the results of detecting the anti-EV71 effect of polypeptide CR in RD cells.
Figure 10:
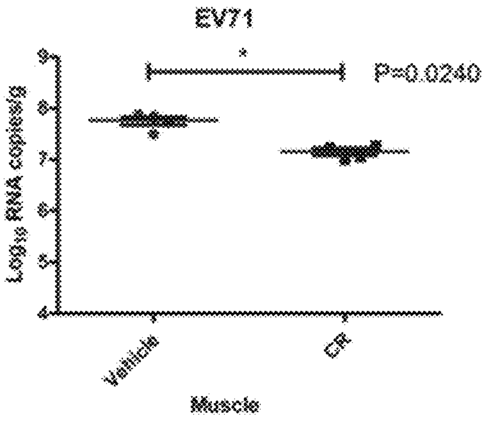
FIG. 10 shows the results of detecting the antiviral activity of polypeptide CR against EV71 in mice.

The results are shown in FIG. 9 and Table 18. The $IC_{50}$ of CR inhibiting EV71 is 1.7 μM.

TABLE 18

| Concentration of polypeptide CR (μM) | Virus inhibition rate (%) | | |
|---|---|---|---|
| 0.15625 | −4.345738 | −7.142856 | −8.595442 |
| 0.3125 | 13.289320 | 2.833130 | 3.745496 |
| 0.625 | 16.422570 | 7.118847 | 16.770710 |
| 1.25 | 50.804320 | 47.503000 | 45.630250 |
| 2.5 | 78.259310 | 70.504210 | 64.429770 |
| 5 | 74.465790 | 71.500600 | 69.255700 |

Example 13

Antiviral Activity of Polypeptide CR against EV71 and CVA16 in Mice

1. Material

Polypeptide CR (sequence: YGRKKRRQRRRGSGCR) was commercially synthesized. Newborn 2-day-old ICR suckling mice were used in the experiment.

2. Antiviral Activity of Polypeptide CR in Mice (1) 8 2-day-old ICR mice were randomly divided into two groups, 4 in each group. The 8 mice were administered EV71 by intraperitoneal injection at a dose of $10^8$ PFU/ml.

(2) At the same time, one group was intraperitoneally injected with 10 mg/kg of polypeptide CR as a treatment group, and the other group was intraperitoneally injected with an equal amount of PBS as a control group.

(3) Polypeptide and PBS were injected every 12 h for 5 days.

(4) At the fifth day, the mice were euthanized, and their hind limb muscle tissues were collected and triturated with Trizol (Invitrogen) to extract total RNA.

(5) Fluorescence quantification experiments were performed using a one step qRT-PCR kit.

The results are shown in FIG. 7 and Table 16. It can be seen that CR can significantly reduce the EV71 viral load in mice.

3. The Procedure for Detecting the Antiviral Activity of CR Against CVA16 in Mice is Similar to the EV71 Experiment.

Figure 11:
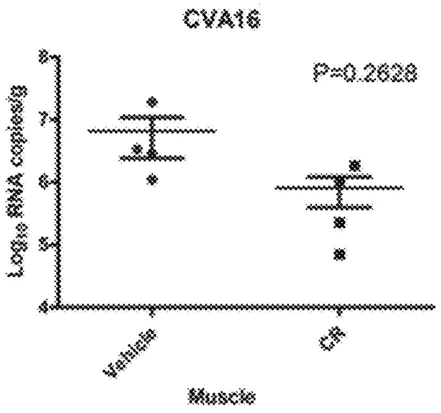
FIG. 11 shows the results of detecting the antiviral activity of polypeptide CR against CVA16 in mice.

The results are shown in FIG. 11 and Table 20. It can be seen that CR can significantly reduce the viral load of CVA16 in mice.

TABLE 19

| Sample | Number of virus copy in muscle tissue (Copies/g) | | | | Significance analysis (treatment vs. control) |
|---|---|---|---|---|---|
| PBS (control) | 3.131500e+007 | 7.089894e+007 | 5.287820e+007 | 7.465289e+007 | P = 0.0240 |
| CR (treatment) | 1.879620e+007 | 1.122332e+007 | 1.738292e+007 | 9852432.0000 | |

TABLE 20

| Sample | Number of virus copies in muscle tissue (Copies/g) | | | | Significance analysis (treatment vs. control) |
|---|---|---|---|---|---|
| PBS (control) | 3310458 | 2870615 | 1076559 | 1.899580e+007 | P = 0.2628 |
| P1 (treatment) | 228883 | 1832418 | 71627 | 1061937 | |

Example 14

Toxicity Evaluation of ER-DRI in Mice

1. Material

Polypeptide ER-DRI was commercially synthesized. Newborn 2-day-old ICR suckling mice were used.

2. Toxicity Evaluation of ER-DRI in Mice (1) A total of 12 10-day-old suckling mice were randomly divided into two groups, 6 in each group. One group was intraperitoneally injected with 20 mg/kg ER-DRI once daily for 3 consecutive days, and the other group was injected with an equal amount of PBS as a control.

(2) The body weight of the mice was recorded daily for a total of 15 days.

(3) Four weeks after the administration, the mice were euthanized and dissected, and the brain, liver, lung, and kidney were collected for HE staining.

Figure 12:
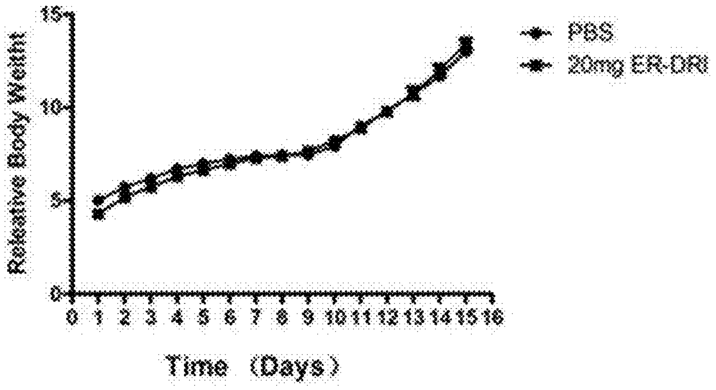
FIG. 12 shows the results of mouse body weight measurement in toxicity evaluation of polypeptide ER-DRI.
Figure 13:
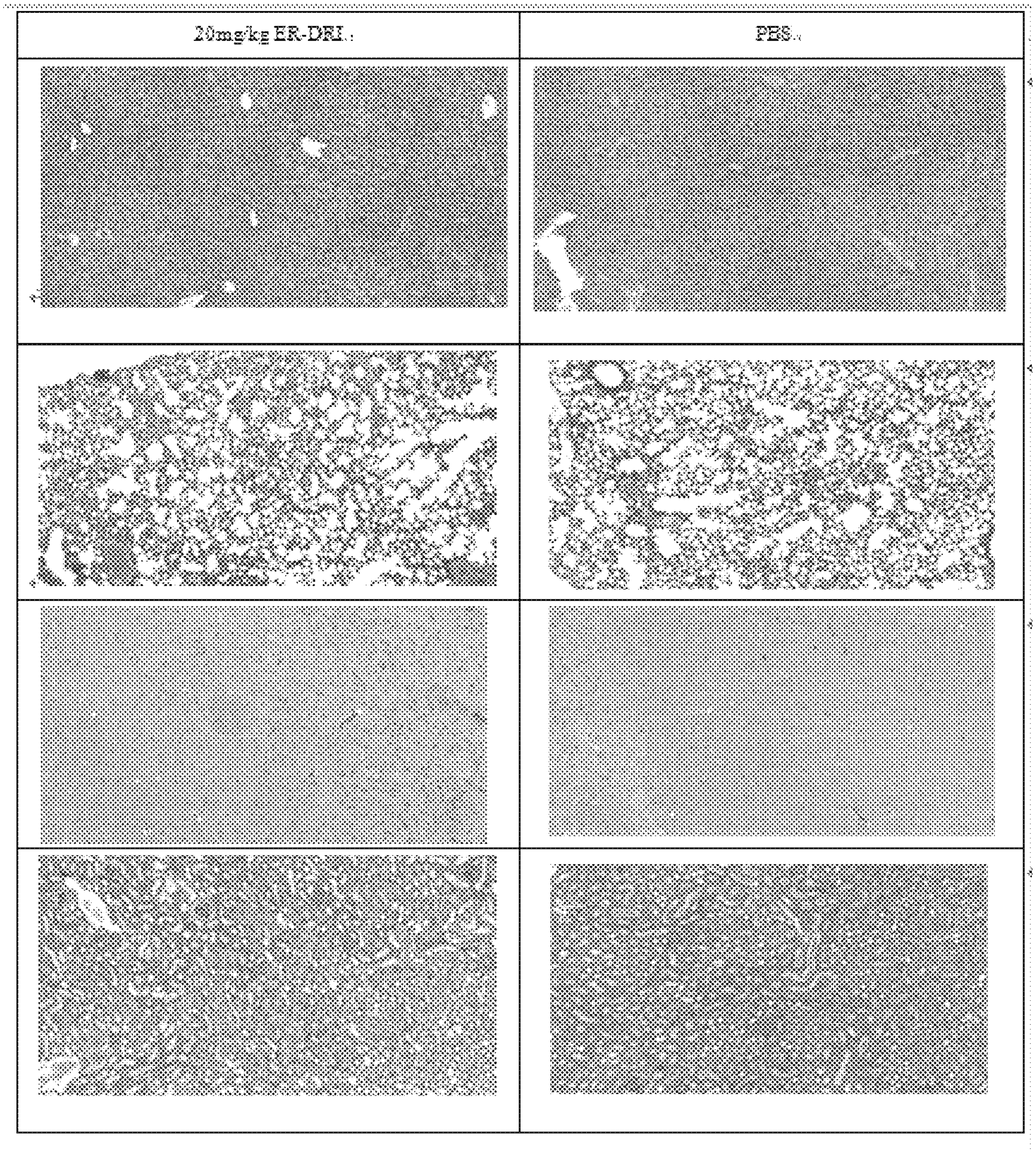
FIG. 13 shows the results of HE staining for toxicity evaluation of polypeptide ER-DRI in mice.

The results are shown in FIG. 12. There is no significant difference in body weight between the 20 mg/kg polypeptide injection group and the PBS group. The HE staining results in FIG. 13 showed that there is no significant pathological change in the brain, liver, lung and kidney of the 20 mg/kg peptide injection group and the PBS group, and there was no significant difference between groups.

Example 15

Toxicity Detection of ER and ER-DRI in RD Cells

1. Experimental Materials

CCK-8 reagent was purchased from MCE.

2. Experiment Procedure

Polypeptides ER and ER-DRI were desired to be able to inhibit viruses, and also to be non-toxic to cells. Therefore, the cytotoxicity test was used for detection, and untreated cells were used as the control group.

The experiment was performed as follows.

(1) RD cells were plated in a 96-well plate at 100 μl per well.

(2) After the cells reached 70%-80% confluence, the MEM medium containing 10% serum was replaced with a MEM medium containing 2% serum. Then, polypeptide ER or ER-DRI was added to generate gradient concentrations of 0.46 μM, 2.34 μM, 4.68 μM, 9.37 μM, 18.75 μM, 37.5 μM, 75 μM, 150 μM, 300 μM (final concentrations), respectively.

(3) The test was performed 24 hours after the addition of the polypeptide, and 10 μl of viable cell detection reagent CCK-8 was added to each well and mixed well.

(4) The plate was incubated at 37° C. for 2 h.

(5) The absorbance value at $OD_{450}$ was measured with a microplate reader.

The results are shown in FIG. 17 and Table 6. Taking the cell viability of untreated cells as 100%, the 50% cytotoxic concentration ($CC_{50}$) of TAT-ER-DRI is calculated to be 117 μM, and the $CC_{50}$ of TAT-ER is calculated to be 290 Therefore, polypeptides ER and ER-DRI have very low toxicity based on the comparison of the 50% cytotoxic concentration (290 μM, 117 μM) and the half-inhibitory activity ($IC_{50}$ 1.26 μM, 0.64 μM).

TABLE 21

| Concentration of polypeptide ER-DRI (μM) | Cell viability (%) | | |
|---|---|---|---|
| 0.46875 | 102.759000 | 100.188600 | 99.276570 |
| 2.34375 | 104.410400 | 98.834360 | 96.326180 |
| 4.6875 | 101.204300 | 98.509610 | 97.632100 |
| 9.375 | 96.049800 | 96.789120 | 94.149670 |
| 18.75 | 95.835600 | 91.144020 | 89.008960 |
| 37.5 | 86.003300 | 86.770260 | 86.970640 |
| 75 | 68.902140 | 70.415330 | 71.949260 |
| 150 | 34.001950 | 34.616900 | 34.084860 |
| 300 | 18.206690 | 17.577920 | 18.690360 |

TABLE 22

| Concentration of ER (μM) | Cell viability (%) | | |
|---|---|---|---|
| 0.46875 | 99.932980 | 99.338760 | 100.043500 |
| 2.34375 | 98.551070 | 98.074300 | 102.662300 |
| 4.6875 | 99.145290 | 100.810500 | 103.132100 |
| 9.375 | 98.530330 | 98.475060 | 102.406600 |
| 18.75 | 98.993280 | 96.588750 | 98.468150 |
| 37.5 | 94.847540 | 95.690510 | 92.235730 |
| 75 | 89.693010 | 89.789740 | 90.356330 |
| 150 | 72.923510 | 74.319240 | 76.716850 |
| 300 | 42.210510 | 43.392040 | 48.408390 |

Example 16

Detection of Antiviral Activity of ER and ER-DRI against EV71 in RD Cells

1. Material

Total RNA extraction kit (Omega), 24-well plate, 100 mm dish, and 50 ml syringe, 0.22 μm filter membrane (Millipore), one step qRT-PCR kit (Takara) were purchased in the market. The water used in the RNA extraction and qRT-PCR was DEPC-treated water, and the entire experiment was carried out in an RNase free environment.

2. Detect Polypeptide Antiviral Efficiency in Cells (1) RD cells in good growth state were plated in a 96-well plate.

(2) After the cells reached 70%-80% confluence, the MEM medium containing 10% serum was replaced with a MEM medium containing 2% serum. Group without polypeptide and virus, and group with virus but without polypeptide were included as controls. The final virus concentration was 0.1 MOI.

(3) 1 h later, polypeptide CR at a final concentration of 2.5 μM, 1.25 μM, 0.625 μM, 0.3125 μM, and 0.15625 μM was added, respectively. Group without polypeptide and virus, and group with virus but without polypeptide were set as controls.

(4) 24 hours after virus infection, when the change in the control group with only virus was obvious, 10 μl of viable cell detection agent CCK-8 was added to each well and mixed well.

(5) The plate was incubated at 37° C. for 2 h.

(6) The absorbance value at $OD_{450}$ was measured with a microplate reader. Inhibition rate of polypeptide=(OD well with treatment−OD well with virus only)×100%/(OD well without treatment−OD well with virus only), OD refers to the value of $OD_{450}$-$OD_{630}$.

Figure 20:
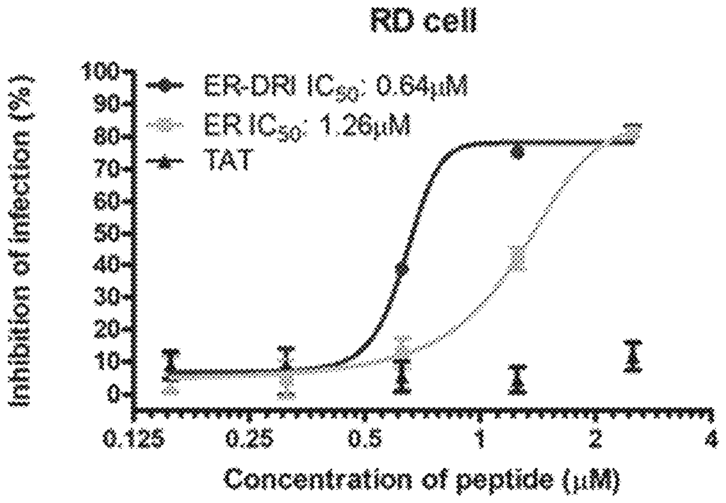
FIG. 20 shows the results of detecting the anti-EV71 effects of ER-DRI and ER in RD cells.

The results are shown in FIG. 20 and Tables 23 to 25. It can be seen that the $IC_{50}$ of ER against EV71 in RD cells is 1.26 μM, and the $IC_{50}$ of ER-DRI against EV71 in RD cells is 0.64

TABLE 23

| Concentration of polypeptide ER-DRI (μM) | Virus inhibition rate (%) | | |
|---|---|---|---|
| 0.15625 | 18.061620 | 2.991017 | −1.026955 |
| 0.3125 | 20.924260 | 2.092426 | −2.130934 |
| 0.625 | 37.804870 | 40.474960 | 37.946090 |
| 1.25 | 75.853660 | 72.426190 | 77.522470 |
| 2.5 | 78.677790 | 85.288830 | 79.756090 |

TABLE 24

| Concentration of polypeptide ER (μM) | Virus inhibition rate (%) | | |
|---|---|---|---|
| 0.15625 | 1.360719 | 0.5905035 | 16.611040 |
| 0.3125 | −1.591784 | −0.1797201 | 15.763800 |
| 0.625 | 8.177150 | 7.432604 | 21.912710 |
| 1.25 | 37.599480 | 40.038510 | 48.844680 |
| 2.5 | 83.453140 | 79.756090 | 80.924260 |

TABLE 25

| Concentration of polypeptide TAT (μM) | Virus inhibition rate (%) | | |
|---|---|---|---|
| 0.15625 | 4.465894 | 4.749035 | 17.426000 |
| 0.3125 | 5.997427 | 8.301158 | 11.634490 |
| 0.625 | −2.908619 | 6.216215 | 12.728440 |
| 1.25 | −0.733587 | 2.162163 | 11.879020 |
| 2.5 | 7.014158 | 7.657658 | 20.115830 |

Example 17

Detection of Antiviral Activity of ER-DRI against EV71 in Mice

1. Experimental Materials

Polypeptide ER-DRI was commercially synthesized. 10 2-day-old suckling mice were used.

2. Experiment Procedure (1) 10 2-day-old ICR mice were randomly divided into two groups, 5 in each group. The 10 mice were administered with EV71 by intraperitoneal injection at a dose of $10^8$ PFU/ml.

(2) At the same time, one group was intraperitoneally injected with 10 mg/kg of polypeptide ER-DRI as a treatment group, and the other group was intraperitoneally injected with an equal amount of PBS as a control group.

(3) Polypeptide and PBS were injected every 12 h for 5 days.

(4) At the fifth day, the mice were euthanized, and their lung tissues were collected and triturated with Trizol (Invitrogen) to extract total RNA.

(5) Fluorescence quantification experiments were performed using a one step qRT-PCR kit.

Figure 21:
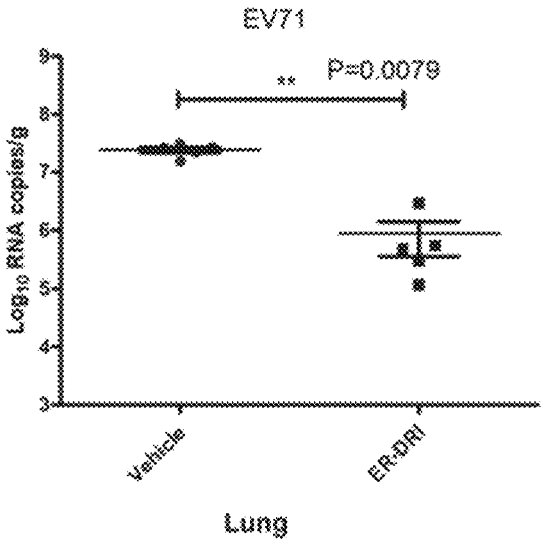
FIG. 21 shows the results of detecting the antiviral activity of polypeptide ER-DRI against EV71 in mice.

The results are shown in FIG. 21 and Table 26. It can be seen that ER-DRI can significantly reduce the viral load of EV71 in the mouse lung.

TABLE 26

| Sample | Number of virus copy in lung tissue (Copies/g) | | | | | Significance analysis (treatment vs. control) |
|---|---|---|---|---|---|---|
| PBS (control) | 2.229596e+007 | 1.550789e+007 | 2.656590e+007 | 2.644002e+007 | 3.103317e+007 | P = 0.0079 |
| ER-DRI (treatment) | 294534 | 484192 | 2956937 | 549759 | 116302 | |

TABLE 27

| Concentration of polypeptide BP8 (μM) | Cell viability (%) | | |
|---|---|---|---|
| 3.0625 | 102.1895 | 103.1369 | 104.4 |
| 6.125 | 101.1158 | 103.5158 | 101.1158 |
| 12.5 | 94.86318 | 99.34739 | 104.8421 |
| 25 | 93.41055 | 97.26318 | 99.85265 |
| 50 | 95.17897 | 94.16844 | 97.64213 |
| 100 | 93.09476 | 93.60002 | 96.25265 |
| 200 | 88.92633 | 93.09476 | 92.08423 |

Example 18

Toxicity of Polypeptides BP8, BP10 and BP15 in RD Cells

1. Experimental Materials

CCK-8 reagent was from MCE.

2. Experimental Procedure

Polypeptides BP8, BP10 and BP15 were desired to be able to inhibit viruses, and also to be non-toxic to cells. Therefore, the cytotoxicity test was used for detection, and untreated cells were used as the control group.

The experiment was performed as follows.

(1) RD cells were plated in a 96-well plate at 100 μl per well.

(2) After the cells reached 70%-80% confluence, the MEM medium containing 10% serum was replaced with a MEM medium containing 2% serum. Then, polypeptide BP8, BP10 or BP15 was added to generate gradient concentrations of 3.0625 μM, 6.125 M, 12.5 μM, 25 μM, 50 μM, 100 μM, and 200 μM (final concentrations), respectively.

(3) The samples were collected 24 hours after the addition of the polypeptide, and 10 μl of live cell detection reagent CCK-8 was added to each well and mixed well.

(4) The plate was placed at 37° C. for 4 h.

(5) The absorbance value at $OD_{450}$ was measured with a microplate reader.

Figure 23:
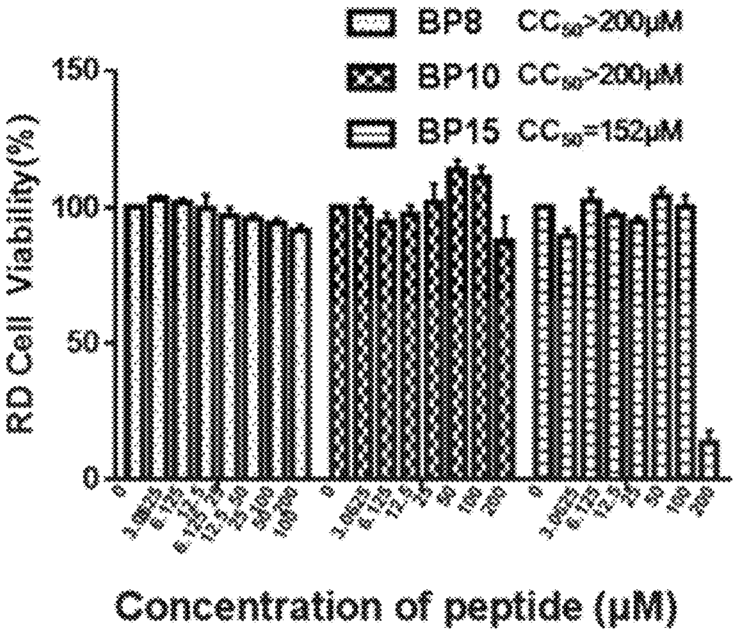
FIG. 23 shows the results of toxicity experiments of polypeptides BP8, BP10 and BP15 in RD cells.

The results are shown in FIG. 23 and Tables 27 to 29. Taking the cell viability of untreated cells as 100%, the cell viability of cells added with 200 μM BP8 and BP10 are substantially the same as that of the control group (untreated cells), the cell viability of cells added with 100 μM BP15 are substantially the same as that of the control group (untreated cells), and the cell viability is decreased to 20% after the addition of 200 μM polypeptide. These results indicate that BP8 and BP10 are not toxic to cells within 200 μM, and BP15 is not toxic to cells within 100 μM.

TABLE 28

| Concentration of polypeptide BP10 (μM) | Cell viability (%) | | |
|---|---|---|---|
| 3.0625 | 97.73014 | 98.99117 | 103.5309 |
| 6.125 | 98.54981 | 93.25347 | 92.62295 |
| 12.5 | 94.82976 | 97.35183 | 100.8827 |
| 25 | 109.4578 | 99.55864 | 96.2169 |
| 50 | 109.1425 | 115.4477 | 116.3934 |
| 100 | 106.8726 | 112.232 | 114.3758 |
| 200 | 79.69735 | 85.18285 | 97.54098 |

TABLE 29

| Concentration of polypeptide BP15 (μM) | Cell viability (%) | | |
|---|---|---|---|
| 3.0625 | 90.96416 | 85.76992 | 91.09402 |
| 6.125 | 103.6901 | 105.7678 | 97.71668 |
| 12.5 | 96.67783 | 98.75552 | 95.24941 |
| 25 | 96.67783 | 92.912 | 95.05463 |
| 50 | 107.391 | 103.6251 | 100.2489 |
| 100 | 96.28826 | 99.4048 | 104.9237 |
| 200 | 9.674276 | 18.37463 | 12.59604 |

Example 19

Toxicity of Polypeptides BP8, BP10 and BP15 in Vero Cells

1. Experimental Materials

CCK-8 reagent was from MCE.

2. Experimental Procedure

Polypeptides BP8, BP10 and BP15 were desired to be able to inhibit viruses, and also to be non-toxic to cells. Therefore, the cytotoxicity test was used for detection, and untreated cells were used as the control group.

The experiment was performed as follows.

(1) Vero cells were plated in a 96-well plate at 100 μl per well.

(2) After the cells reached 70%-80% confluence, the MEM medium containing 10% serum was replaced with a MEM medium containing 2% serum. Then, polypeptide BP8, BP10 or BP15 was added to generate gradient concentrations of 3.0625 μM, 6.125 M, 12.5 μM, 25 μM, 50 μM, 100 μM, and 200 μM (final concentrations), respectively.

(3) The samples were collected 24 hours after the addition of the polypeptide, and 10 μl of live cell detection reagent CCK-8 was added to each well and mixed well.

(4) The plate was placed at 37° C. for 4 h.

(5) The absorbance value at $OD_{450}$ was measured with a microplate reader.

Figure 24:
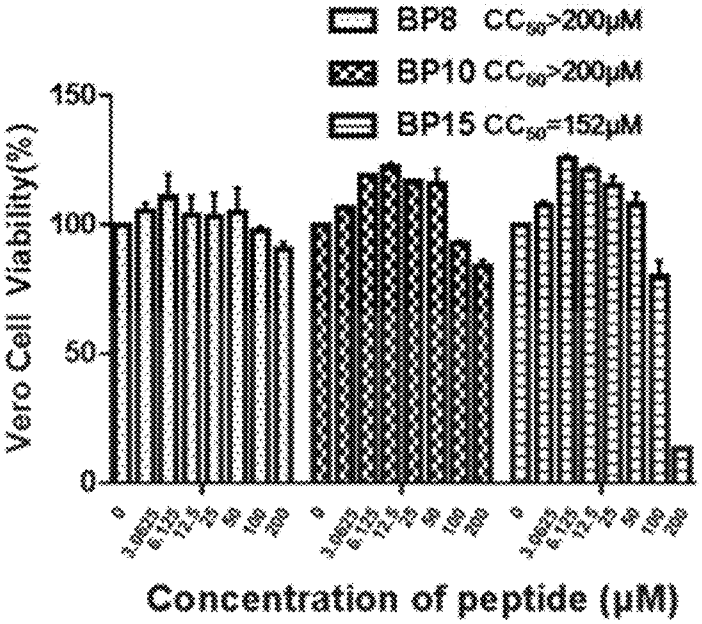
FIG. 24 shows the results of toxicity experiments of polypeptides BP8, BP10 and BP15 in Vero cells.

The results are shown in FIG. 24 and Tables 30, 31 and 32. Taking the cell viability of untreated cells as 100%, the cell viability of cells added with 200 μM BP8 and BP10 are substantially the same as that of the control group (untreated cells), the cell viability of cells added with 100 μM BP15 are substantially the same as that of the control group (untreated cells), and the cell viability is decreased to 20% after the addition of 200 μM polypeptide. It indicates that BP8 and BP10 are not toxic to cells within 200 μM, and BP15 is not toxic to cells within 100 μM. The toxicities of the polypeptides in RD cells and Vero cells are relatively consistent.

TABLE 30

| Concentration of polypeptide BP8 (μM) | Cell viability (%) | | |
|---|---|---|---|
| 3.0625 | 103.2048 | 105.2007 | 108.7417 |
| 6.125 | 101.4665 | 111.3814 | 119.3004 |
| 12.5 | 95.54333 | 106.8102 | 109.1924 |
| 25 | 96.63783 | 99.47065 | 113.6348 |
| 50 | 94.44883 | 108.2266 | 112.4759 |
| 100 | 99.6638 | 96.70221 | 97.34603 |
| 200 | 87.23801 | 92.0023 | 92.51736 |

TABLE 31

| Concentration of polypeptide BP10 (μM) | Cell viability (%) | | |
|---|---|---|---|
| 3.0625 | 106.5527 | 106.2952 | 107.1965 |
| 6.125 | 118.8497 | 119.236 | 118.9785 |
| 12.5 | 121.7469 | 120.8456 | 123.9359 |
| 25 | 116.7895 | 117.3689 | 116.0169 |
| 50 | 109.1924 | 118.399 | 120.0086 |
| 100 | 92.77489 | 92.32421 | 94.06254 |
| 200 | 83.05316 | 86.72295 | 82.21619 |

TABLE 32

| Concentration of polypeptide BP15 (μM) | Cell viability (%) | | |
|---|---|---|---|
| 3.0625 | 107.6472 | 105.9733 | 109.128 |
| 6.125 | 125.3523 | 127.0907 | 124.0647 |
| 12.5 | 121.5538 | 120.3949 | 122.777 |
| 25 | 116.2744 | 111.0595 | 118.2059 |
| 50 | 111.5101 | 109.4499 | 102.9473 |
| 100 | 75.77796 | 87.10925 | 76.80808 |
| 200 | 13.64905 | 13.13399 | 13.4559 |

Example 20

Test Antiviral Effect of Polypeptides BP8, BP10 and BP15 against CVB5 in RD Cells 1. Materials Polypeptides BP8 (shown as SEQ ID NO: 12), BP10 (shown as SEQ ID NO: 13), and BP15 (shown as SEQ ID NO: 14) were all commercially synthesized.

2. Antiviral Efficiency of Polypeptides BP8, BP10 and BP15

(1) DR cells were plated in a 24-well cell plate.

(2) After the cells reached 70%-80% confluence, the MEM medium containing 10% serum was replaced with a MEM medium containing 2% serum (0.5 ml/well). CVB5 viruses were added at MOI=0.01, and the group without CVB5 as control.

(3) After 1 h, polypeptides BP8, BP10 or BP15 was added at a final concentration of 0.78 μM, 1.56 μM, 3.13 μM and 6.25 μM, respectively.

(4) Samples were collected 24 hours after virus infection, and RNA was extracted with total RNA extraction kit as follows.

(5) The supernatant in the wells was discarded, then 350 μl of TRK Lysis Buffer was added to each well and the plate was shaken on the shaker for 5 minutes.

(6) 350 μl of 70% ethanol (DEPC-treated) was added to the well and the plate was shaken on the shaker for 5 minutes.

(7) The mixture in the well was transferred to a RNA extraction column and centrifuged at 12000 g for 1 min.

(8) The solution collected in the recovery tube was added back to the column and centrifuged at 12000 g for 1 min.

(9) RNA washing buffer 1 was added to the column and centrifuged at 12,000 g for 30 s.

(10) RNA washing buffer 2 was added to the column and centrifuged at 12,000 g for 1 min.

(11) Step (10) was repeated once.

(12) The column was centrifuged at 12,000 g for 2 min to completely remove residual RNA washing buffer.

(13) 50 μl DEPC-treated $H_2O$ was added to the column and centrifuge at 12,000 g for 2 min.

(14) 2 μl RNA sample was used according to one step qRT-PCR kit for fluorescence quantification experiment.

Figure 25:
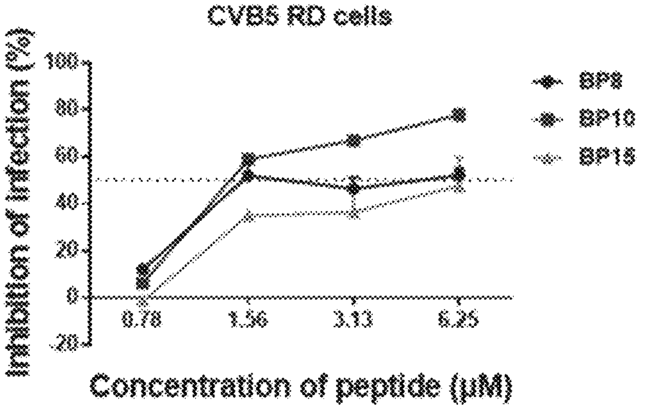
FIG. 25 shows the results of detecting the anti-CVB5 effect of polypeptides BP8, BP10 and BP15 in RD cells.

The results are shown in FIG. 25 and Tables 33, 34 and 35. It can be seen that the polypeptides BP8, BP10 and BP15 all can significantly inhibit CVB5. The $IC_{50}$ of BP8 is 1.545 μM, the $IC_{50}$ of BP10 is 1.335 μM, and the $IC_{50}$ of BP15 is 6.758 μM.

TABLE 33

| Concentration of polypeptide BP8 (μM) | Virus inhibition rate (%) | | |
|---|---|---|---|
| 0.78 | 12.95326 | 11.39885 | 10.25664 |
| 1.56 | 55.69942 | 47.92739 | 42.01265 |
| 3.13 | 51.42481 | 41.70977 | 45.98439 |
| 6.25 | 50.21543 | 54.14502 | 49.8704 |

TABLE 34

| Concentration of polypeptide BP10 (μM) | Virus inhibition rate (%) | | |
|---|---|---|---|
| 0.78 | 6.347029 | 6.12571 | 5.45871 |
| 1.56 | 58.80824 | 54.23212 | 56.01254 |
| 3.13 | 65.56288 | 66.96887 | 67.23652 |
| 6.25 | 78.62692 | 77.07251 | 76.12545 |

TABLE 35

| Concentration of polypeptide BP15 (μM) | Virus inhibition rate (%) | | |
|---|---|---|---|
| 0.78 | −1.81361 | 0.13541 | −0.25921 |
| 1.56 | 30.95842 | 35.10354 | 33.44521 |
| 3.13 | 43.26418 | 29.66312 | 37.15236 |
| 6.25 | 56.08803 | 38.98956 | 46.59892 |

Example 21

Test Antiviral Effect of Polypeptide BP8 against CVB3 in Vero Cells

1. Materials

Polypeptides BP8 (shown as SEQ ID NO: 12) was commercially synthesized.

2. Anti-CVB3 Effect of Polypeptide BP8

(1) Vero cells were plated in a 24-well cell plate.

(2) After the cells reached 70%-80% confluence, the MEM medium containing 10% serum was replaced with a MEM medium containing 2% serum and CVB3 virus, 0.5 ml per well. MOI of the virus was 0.01. Wells without CVB3 virus was set as control group.

(3) After 1 h, polypeptide BP8 was added at a final concentration of 0.25 μM, 0.5 μM and 10 μM, respectively.

(4) Samples were collected 24 hours after virus infection, and RNA was extracted with total RNA extraction kit as follows.

(5) The supernatant in the wells was discarded, then 350 μl of TRK Lysis Buffer was added to each well and the plate was shaken on the shaker for 5 minutes.

(6) 350 μl of 70% ethanol (DEPC-treated) was added to the well and the plate was shaken on the shaker for 5 minutes.

(7) The mixture in the well was transferred to a RNA extraction column and centrifuged at 12000 g for 1 min.

(8) The solution collected in the recovery tube was added back to the column and centrifuged at 12000 g for 1 min.

(9) RNA washing buffer 1 was added to the column and centrifuged at 12,000 g for 30 s.

(10) RNA washing buffer 2 was added to the column and centrifuged at 12,000 g for 1 min.

(11) Step (10) was repeated once.

(12) The column was centrifuged at 12,000 g for 2 min to completely remove residual RNA washing buffer.

(13) 50 μl DEPC-treated $H_2O$ was added to the column and centrifuge at 12000 g for 2 min.

(14) 2 μl RNA sample was used according to one step qRT-PCR kit for fluorescence quantification experiment.

Figure 26:
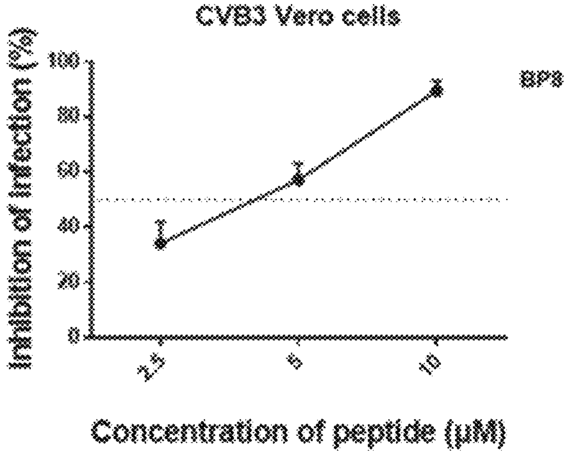
FIG. 26 shows the results of detecting the anti-CVB3 effect of polypeptide BP8 in Vero cells.

The results are shown in FIG. 26 and Table 36. It can be seen that polypeptide BP8 is able to inhibit the replication of CVB3. The $IC_{50}$ of BP8 is 4.125 μM.

TABLE 36

| Concentration of polypeptide BP8 (μM) | Virus inhibition rate (%) | | |
|---|---|---|---|
| 2.5 | 40.9035 | 25.50707 | 36.01721 |
| 5 | 64.04425 | 53.44192 | 54.17947 |
| 10 | 87.83036 | 86.81623 | 93.6386 |

Example 22

Test Antiviral Effect of Polypeptide BP8 against CVB5 in Mice

1. Materials: Polypeptide BP8 (shown as SEQ ID NO: 12) was commercially synthesized. 10 2-day-old ICR suckling mice were used.

2. Antiviral activity of peptide BP8 in mice (1) 10 2-day-old ICR suckling mice were randomly divided into two groups, 5 in each group. The 10 suckling mice were challenged by intraperitoneal injection of CVB5 at a dose of $10^8$ PFU/ml.

(2) At the same time, one group was intraperitoneally injected with 10 mg/kg of polypeptide BP8 as a treatment group, and the other group was intraperitoneally injected with an equal amount of PBS as a control group.

(3) Polypeptide and PBS were injected every 12 h for 5 days.

(4) At the fifth day, the mice were euthanized, and their hind limb muscle tissues were collected and triturated with Trizol (Invitrogen) to extract total RNA.

(5) Fluorescence quantification experiments were performed using a one step qRT-PCR kit.

Figure 27:
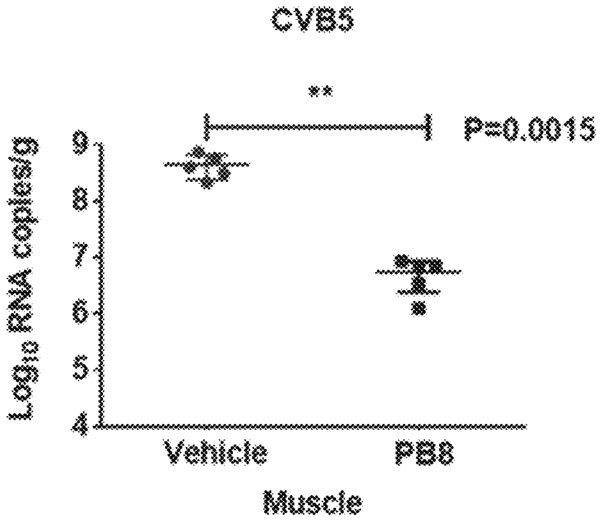
FIG. 27 shows the results of detecting the anti-CVB5 effect of polypeptide BP8 in mice.

The results are shown in FIG. 27 and Table 37. It can be seen that virus copy number in the treatment group (BP8) is significantly lower than that of the blank control group (PBS) by nearly 80 times.

TABLE 37

| Sample | Number of virus copy in muscle tissue (Copies/g) | | | | | Significance analysis (treatment vs. control) |
|---|---|---|---|---|---|---|
| Vehicle (control) | 2.15e+008 | 3.16e+008 | 5.78e+008 | 4e+008 | 7.41e+008 | P = 0.0015 |
| BP8 (treatment) | 3.43e+006 | 7.00 + 006 | 8.53e+006 | 7.03e+006 | 1.24e+006 | |

Example 23

Detection of Antiviral Effect of Polypeptide ER-DRI against CVA6 in Vero Cells

1. Materials

Polypeptide ER-DEI (SEQ ID NO: 11) was commercially synthesized.

2. Anti-CVA6 Effect of Polypeptide ER-DEI (1) Vero cells were plated in a 24-well cell plate.

(2) After the cells reached 70%-80% confluence, the MEM medium containing 10% serum was replaced with a MEM medium containing 2% serum and CVA6 virus, 0.5 ml per well. MOI of the virus was 0.01. The wells without CVA6 virus was set as control group.

(3) After 1 h, polypeptide ER-DRI was added at a final concentration of 2.5 μM, 5 μM and 10 μM, respectively.

(4) Samples were collected 24 hours after virus infection, and RNA was extracted with total RNA extraction kit as follows.

(5) The supernatant in the wells was discarded, then 350 μl of TRK Lysis Buffer was added to each well and the plate was shaken on the shaker for 5 minutes.

(6) 350 μl of 70% ethanol (DEPC-treated) was added to the well and the plate was shaken on the shaker for 5 minutes.

(7) The mixture in the well was transferred to a RNA extraction column and centrifuged at 12000 g for 1 min.

(8) The solution collected in the recovery tube was added back to the column and centrifuged at 12000 g for 1 min.

(9) RNA washing buffer 1 was added to the column and centrifuged at 12,000 g for 30 s.

(10) RNA washing buffer 2 was added to the column and centrifuged at 12,000 g for 1 min.

(11) Step (10) was repeated once.

(12) The column was centrifuged at 12,000 g for 2 min to completely remove residual RNA washing buffer.

(13) 50 μl DEPC-treated $H_2O$ was added to the column and centrifuge at 12,000 g for 2 min.

(14) 2 μl RNA sample was used according to one step qRT-PCR kit for fluorescence quantification experiment.

Figure 28:
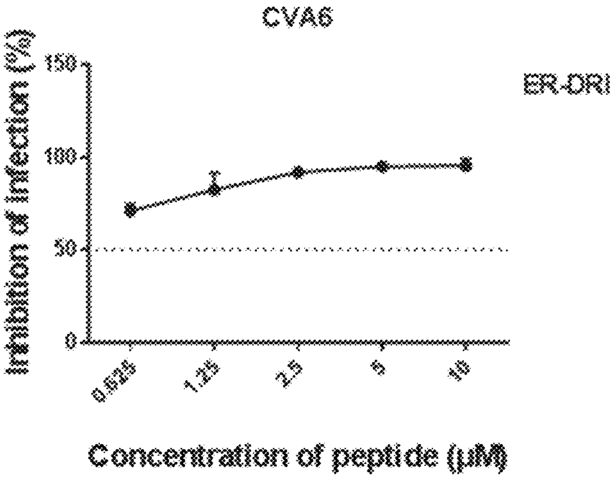
FIG. 28 shows the results of detecting the anti-CVA6 effect of polypeptide ER-DRI in Vero cells.

The results are shown in FIG. 28 and Table 38. It can be seen that polypeptide ER-DRI is able to inhibit the replication of CVA6. The $IC_{50}$ of ER-DRI is less than 0.625 μM.

TABLE 38

| Concentration of polypeptide ER-DRI (μM) | Virus inhibition rate (%) | | |
|---|---|---|---|
| 0.625 | 71.8 | 74.9 | 67.5 |
| 2.15 | 72.6 | 85.3 | 90.4 |
| 2.5 | 91.3 | 93.4 | 91.7 |
| 5 | 94.3 | 94.9 | 96.4 |
| 10 | 91.4 | 97.8 | 97.9 |

The polypeptides and application thereof provided by the present invention are described in detail above. The principles and embodiments of the present invention have been described with reference to specific examples, and the description of the above embodiments is only to assist in understanding the method of the present invention and the core idea thereof. It should be noted that those skilled in the art can make various modifications and changes to the present invention without departing from the spirit and scope of the invention.

What is claimed is:

1. A polypeptide capable of inhibiting the activity of enterovirus protein 3A, wherein the polypeptide consists of a sequence selected from the group consisting of SEQ ID NOs: 2 to 14.

2. A nucleic acid encoding the polypeptide of claim 1.

3. A medicine comprising the polypeptide according to claim 1 and pharmaceutically acceptable excipients.

4. An inhibitor of enterovirus, wherein the inhibitor is polypeptide P2 with the amino acid sequence shown in SEQ ID NO: 2.

5. A variant of an inhibitor of enterovirus, wherein the variant is 3A-TAT-EP with the amino acid sequence as shown in SEQ ID NO: 3, 3A-EP-DRI with the amino acid sequence as shown in SEQ ID NO: 4, or 3A-EP-PEG4-PA with the amino acid sequence as shown in SEQ ID NO: 5.

6. A method of treating a disease caused by enterovirus, comprising administering the polypeptide according to claim 1 to a subject in need thereof;

wherein the enterovirus belongs to the Picornaviridae enterovirus genus, including human Enterovirus (EV), Coxsackie A virus (CVA), Coxsackie B virus (CVB), Echovirus, Rhinovirus and Poliovirus;

and the disease is selected from hand-foot-and-mouth disease, myocarditis, herpes angina, aseptic meningitis, encephalitis and viral cold.

7. The polypeptide of claim 1, which is polypeptide P2 with the amino acid sequence shown in SEQ ID NO: 2.

8. The polypeptide of claim 1, which is 3A-TAT-EP with the amino acid sequence as shown in SEQ ID NO: 3, 3A-EP-DRI with the amino acid sequence as shown in SEQ ID NO: 4, or 3A-EP-PEG4-PA with the amino acid sequence as shown in SEQ ID NO: 5.

9. The polypeptide of claim 1, wherein the polypeptide is set forth in SEQ ID NO: 10.

* * * * *